(12) United States Patent
Gadegaard et al.

(10) Patent No.: US 10,768,175 B2
(45) Date of Patent: Sep. 8, 2020

(54) PLASMONIC DEVICE, METHOD OF MANUFACTURING A PLASMONIC DEVICE AND METHOD OF ANALYSIS USING A PLASMONIC DEVICE

(71) Applicant: THE UNIVERSITY COURT OF THE UNIVERSITY OF GLASGOW, Glasgow (GB)

(72) Inventors: Nikolaj Holledig Gadegaard, Glasgow (GB); Affar Shahid Karimullah, Glasgow (GB); Malcolm Kadodwala, Glasgow (GB)

(73) Assignee: The Univ. Court of the Univ. of Glasgow, Glasgow (GB)

( * ) Notice: Subject to any disclaimer, the term of this patent is extended or adjusted under 35 U.S.C. 154(b) by 323 days.

(21) Appl. No.: 15/630,524

(22) Filed: Jun. 22, 2017

(65) Prior Publication Data

US 2017/0370923 A1 Dec. 28, 2017

(30) Foreign Application Priority Data

Jun. 23, 2016 (GB) .................................... 1610991.0

(51) Int. Cl.
*G01N 21/00* (2006.01)
*G01N 33/543* (2006.01)
(Continued)

(52) U.S. Cl.
CPC ....... *G01N 33/54373* (2013.01); *G01N 21/27* (2013.01); *G01N 21/554* (2013.01);
(Continued)

(58) Field of Classification Search
CPC ........................... G01N 21/554; G01N 21/553
(Continued)

(56) References Cited

U.S. PATENT DOCUMENTS

2008/0218761 A1* 9/2008 Nishikawa ........... G01N 21/554
356/445
2011/0141541 A1* 6/2011 Bratkovski ............ G02B 1/005
359/240

OTHER PUBLICATIONS

A.C. Liou 2006, Injection molding of polymer micro; *Int J Adv Manuf Technol;* 7 pages.
(Continued)

*Primary Examiner* — Natalia Levkovich
(74) *Attorney, Agent, or Firm* — Adsero IP

(57) ABSTRACT

A plasmonic device is disclosed, the plasmonic device having a base substrate and an electrically conductive film formed on the base substrate. The base substrate has a reference upper surface and an arrangement of chiral nanostructures formed in relief from the reference upper surface. Each chiral nanostructure has a nanostructure upper surface which is disposed at a distance of at least 30 nm from the reference upper surface in a thickness direction. The electrically conductive film is formed on the nanostructure upper surface of each chiral nanostructure and on at least part of the reference upper surface of the base substrate. Also disclosed is a method of analysis of a biological material using the plasmonic device, by depositing the biological material onto the plasmonic device and irradiating the plasmonic device and the biological material with electromagnetic radiation. The arrangement of chiral nanostructures and electrically conductive film generates a superchiral electromagnetic field, the effect of the presence of the biological material on the superchiral electromagnetic field then being detected.

7 Claims, 17 Drawing Sheets

(51) Int. Cl.
  *G01N 21/552* (2014.01)
  *G02B 5/30* (2006.01)
  *G02B 1/00* (2006.01)
  *G01N 21/27* (2006.01)
  *G02B 5/00* (2006.01)

(52) U.S. Cl.
  CPC .............. *G02B 1/002* (2013.01); *G02B 5/008* (2013.01); *G02B 5/3058* (2013.01)

(58) Field of Classification Search
  USPC ........................................ 422/82.05; 436/805
  See application file for complete search history.

(56) References Cited

OTHER PUBLICATIONS

Anker et al. 2008, Biosensing with plasmonic nanosensors; 12 pages.
Belotelov et al. 2013, Plasmon-mediated magneto-optical transparency; 7 pages.
Berini 2000, Plasmon-polariton waves guided by thin lossy metal films, 20 pages.
C.W. Deutsche et al.—Optical Activity, Annual Review; 42 pages.
Cao et al. 2014, Fast tuning of double Fano resonance; Science Reports; 9 pages.
Chen et al., Nanoimprint lithography for planar chiral photonic metamaterial, 6 pages.
E. Hendry, 2010, Chiral Electromagnetic Fields; Nano Letters, 5 pages.
E. Hutter, 2004, Exploitation of LSPR; Advanced Materials; 22 pages.
Gadegaard et al., 2006, Nano patterned surfaces for biomaterial applications, Adv Sci Technol, 9 pages.
Gallinet et al. 2012, Fano resonant plasmonic systems: Functioning principles and applications, 3pages.
Gansel et al. 2009, Gold helix photonic metamaterial as broadband circular polarizer, Sci Mag, 4 pages.
Giannini et al. 2011, Fano resonances in nanoscale plasmonic systems, Nano Letters, 6 pages.
Guerreiro et al. 2014, Multifunctional Biosensor Based on Localized Surface Plasmon Resonance for Monitoring Small Molecule—Protein Interaction, 10 pages.
H. Sun 2014, Recent progress in low temperature nanoimprint lithography; Micro Tech, 7 pages.
Hentschel et al. 2013, Babinet to the Half Coupling of Solid and Inverse Plasmonic Structures, 6 pages.
Huang et al., Plasmonic photothermal therapy, 12pages.
Jack et al., Spatial control of chemical processes, 8 pages.
J.M. Stormonth-Darling 2014, Injection moulding of ultra high aspect ratio, 13 pages.
K.A. Willets et al 2014, Localized Surface Plasmon Resonance Spectroscopy and Sensing 33 pages.
K. Monkkonen et al. 2002, Replication of sub-micron features using amorphous thermoplastics, 9 pages.
Karimullah et al. 2015, Disposable Plasmonics Plastic Templated Plasmonic Metamaterials; Advanced Materials, 7 pages.
Lalanne et al., 2005, Theory of surface plasmon generation at nanoslit apertures, 4 pages.
L. D. Barron, 2009, Molecular Light Scattering and Optical Activity, Cambridge University Press, New York, 37 pages.
Liu et al., 2008—Surface plasmon generation by subwavelength isolated objects, Quantum Electronics, 8 pages.
Liu et al., 2011—Three-dimensional plasmon rulers, 5 pages.
Luk'yanchuk et al.—2010—The Fano resonance in plasmonic nanostructures and metamaterials, Nat Materials, 9 pages.
M. Matschuk, 2013, Injection molding of high aspect ratio sub-100nm nanostructures, 11pages.
Maier, Plasmonics Fundamentals and Applications, Springer US. 2007, 18 pages.
P. B. Johnson et al., 1972—Optical constants of nobel metals, Johnson & Christy, 10 pages.
Pendry, 2004, A chiral route to negative refraction, 4 pages.
P. K. Jain et al., 2007, Review of Some Interesting Surface Plasmon Resonance, 12 pages.
Pranov et al., On the injection molding of nanostructured polymer surfaces, 12 pages.
Prodan et al., 2003, A hybridization model, 5 pages.
P. W. Atkins et al., 2011, Molecular Quantum Mechanics An Introduction to Quantum Chemistry, Oxford University Press, New York, 31 pages.
Shalaev, 2007, Optical negative index metamaterials, 8 pages.
Tsakmakidis et al., 2007, Trapped_rainbow_storage, 5 pages.
Tullius et al., Superchiral Spectroscopy Detection of Protein Higher Order Hierarchical Structure with Chiral, 4 pages.
Valev et al., Chirality and Chiroptical Effects in Plasmonic Nanostructures Fundamentals, 18 pages.
Vora et al., 2014, Exchanging Ohmic losses in metamaterial absorbers, 13 pages.
Yin et al., Interpreting Chiral Nanophotonic Spectra the Plasmonic Born Kuhn Model, 6 pages.

\* cited by examiner

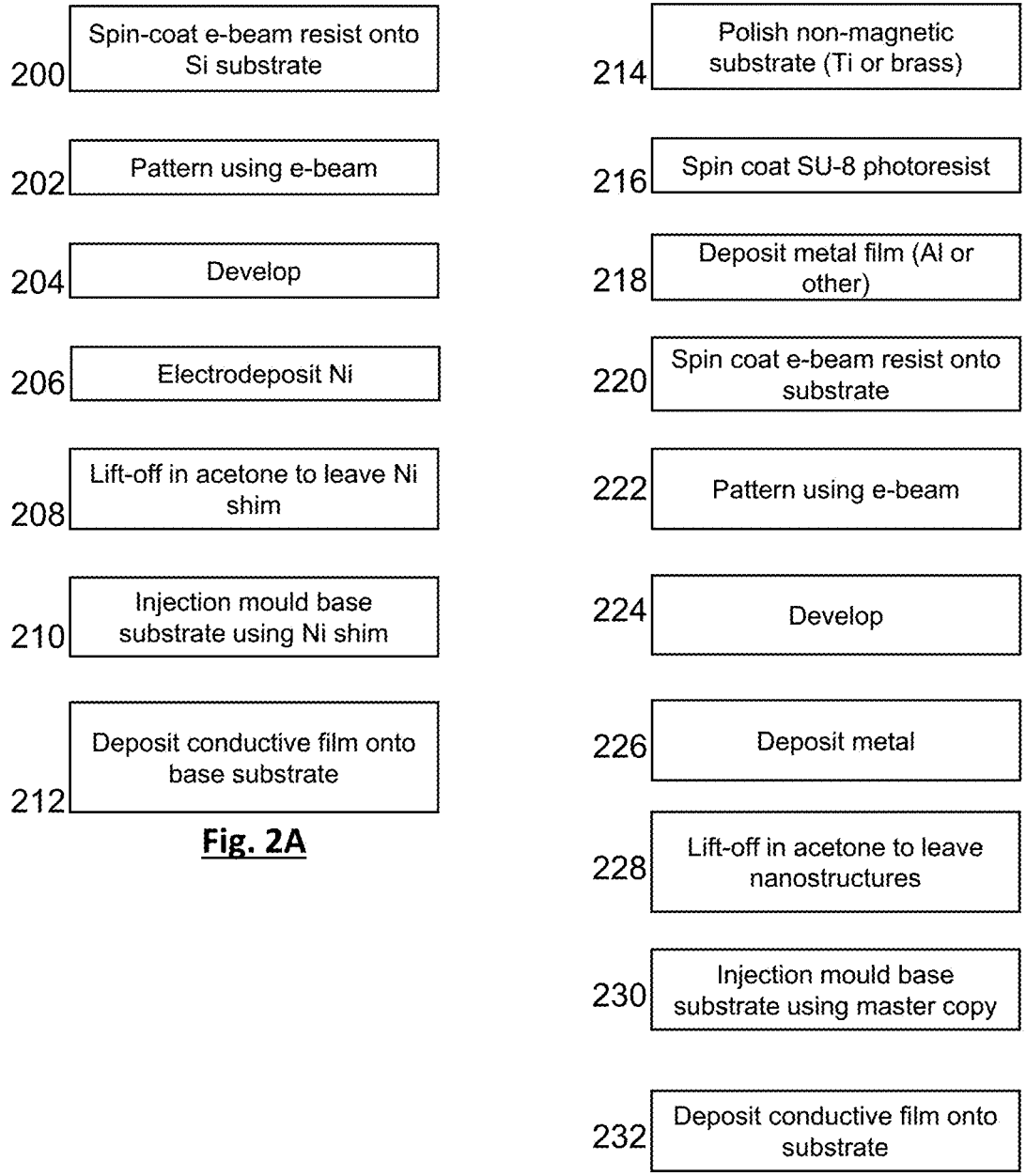

$E_1$ $E_2$

PLASMONIC DEVICE, METHOD OF MANUFACTURING A PLASMONIC DEVICE AND METHOD OF ANALYSIS USING A PLASMONIC DEVICE

CROSS REFERENCE TO RELATED APPLICATIONS

This application claims priority of Great Britain Patent Application No. 1610991.0, filed on Jun. 23, 2016, by Nikolaj Holledig GADEGAARD et al. and titled, "PLASMONIC DEVICE, METHOD OF MANUFACTURING A PLASMONIC DEVICE AND METHOD OF ANALYSIS USING A PLASMONIC DEVICE", which is hereby incorporated by reference in its entirety.

BACKGROUND TO THE INVENTION

Field of the Invention

The present invention relates to a plasmonic device, a method of manufacturing a plasmonic device, and a method of analysis using a plasmonic device, with particular application to the analysis of biological material.

Related Art

Assays and bioassays are useful procedures for measuring the presence, amount, or functional activity, of an analyte. The analyte may be a drug, or a biological material such as a protein. Assays are particularly useful for studying the biological interactions between new pharmaceutical compounds and biological material, for example.

Many techniques for probing the structure of biological materials are known. These include chemical assay, protein crystallography, nuclear magnetic resonance (NMR) spectroscopy and electron microscopy.

Lower-order (primary and secondary) structure of biological material can be probed by a variety of assay techniques. Protein crystallography, NMR and electron microscopy are commonly used to probe higher-order (tertiary and quaternary) structure of biological material, where tertiary structure generally relates to the three-dimensional structure of molecules, and quaternary structure generally relates to the orientation and conformation of proteins.

A problem with protein crystallography, NMR and electron microscopy, is that they are time-consuming, with a low throughput. Large quantities of biological material are also required to perform these measurements to a sufficient degree of accuracy.

Optical spectroscopic methods provide a more scalable alternative for performing assays. However, many optical spectroscopic methods struggle to characterize higher-order (tertiary and quaternary) structure of biological materials.

Another problem with many existing assay techniques, is that they require labelling, such as fluorescent labelling, of analyte materials.

SUMMARY OF THE INVENTION

Recently, new techniques for the spectroscopic analysis of both lower-order and higher-order structure of biological material have been developed, using superchiral electromagnetic fields.

Electromagnetic radiation interacting with the surface of an electrically conductive material can cause free electrons in the conductive material to oscillate as plasmons. These plasmons give rise to evanescent fields which can in turn interact with the electromagnetic radiation causing them. For example, when electromagnetic radiation is incident upon an electrically conductive surface, the reflected radiation can be altered by the presence of plasmons. Changes in the dielectric properties of an electrically conductive material can therefore cause changes in the properties of the reflected electromagnetic radiation.

It has been found that chiral nanostructures—that is, structures on the sub-micrometer scale, and having a chiral shape—can lead to an effect known as superchirality in electromagnetic fields. A superchiral electric field expresses chirality on a shorter length scale than circularly polarized light, at a given wavelength. In effect, superchiral electromagnetic fields "twist" on a shorter length scale than circularly polarized light, at a given wavelength.

Scattering of electromagnetic radiation near chiral nanostructures generates superchiral evanescent fields, the handedness of which depends on the handedness of the chiral nanostructures. For example, light scattering from left-handed chiral nanostructures obtains left-handed superchirality.

This superchirality can be detected in the far-field optical properties of the reflected light, using optical rotatory dispersion (ORD) spectra. An ORD spectra is a plot of optical rotation of the polarization an electromagnetic field, as a function of wavelength. ORD values are generally measured as a change in rotation of electromagnetic radiation at a given wavelength, between an incident beam and a scattered beam.

Biological materials, such as protein and DNA, display chirality on a range of scales, providing potential fingerprints of protein structure over the full range of hierarchical structure. Circularly polarized electromagnetic radiation is sensitive to lower-order (primary and secondary) structure, while the superchiral evanescent fields produced by chiral nanostructures are more sensitive to higher-order (tertiary and quaternary) structure.

Higher order structures of proteins generally display chirality on length scales of 10-100 nm. Without wishing to be bound by theory, it is thought that this sensitivity is due to higher-order biological materials displaying chirality on a similar length scale to the superchiral evanescent fields produced by these chiral nanostructures. Sensitivity arises from the fact that chiral molecules are birefringent, and interact with electromagnetic fields differently based on the handedness of the electromagnetic field.

Because of this birefringence, plasmonic polarimetry measurements can be made using chiral nanostructures, by measuring the asymmetry between the refractive index of a chiral material (e.g. biological material, such as a protein) on a left-handed chiral nanostructure (having a left-handed evanescent field), and on a right-handed chiral nanostructure (having a right-handed evanescent field).

The effect of this asymmetry can be detected through far-field measurements, such as optical rotatory dispersion (ORD). ORD measurements can be made by comparing the ORD spectra of a chiral material on a left-handed chiral nanostructure, with the ORD spectra of the same chiral material on a right-handed chiral nanostructure. The wavelength-shift between ORD spectra of the left-hand chiral nanostructure ($\Delta\lambda_L$) and the right-hand chiral nanostructure ($\Delta\lambda_R$), gives us a dissymmetry/asymmetry factor, $\Delta\Delta\lambda$:

$$\Delta\Delta\lambda = \Delta\lambda_R - \Delta\lambda_L$$

As will be clear to the skilled person, the dissymmetry/asymmetry factor will only be non-zero when a chiral material is used, due to the disparity between $\Delta\lambda_L$ and $\Delta\lambda_R$.

This dissymmetry/asymmetry factor is dependent on the chirality of the chiral media, and can be used to determine structural information about chiral materials, such as proteins.

In addition to ORD spectra, it has been shown that reflectivity spectra can be used to detect changes in protein structure. In particular, when changes in ORD spectra occur, corresponding changes in reflectivity spectra are observed (this can be seen in FIG. 7). Such changes in reflectivity spectra are also the result of birefringence-related effects.

Hence, reflectivity can be used in addition to ORD spectra, in order to accurately measure higher-order protein structure.

Research has shown that the sensitivity of such techniques is sufficient to measure ligand-induced changes in protein conformation.

Research has also shown that it is possible, through the use of such plasmonic devices, to characterize biological materials using only very small quantities of the biological material, without the use of labelling, such as fluorescent labelling.

Aside from use in characterizing biological materials, such plasmonic devices are considered to have potential application to fields such as data storage, and photovoltaic technologies.

A significant problem with the existing plasmonic polarimetry research and technology, is the cost of producing chiral nanostructures for use in measurements. Presently, devices for use in plasmonic polarimetry are manufactured using lithography processes, such as electron beam lithography (EBL) [5]. The resulting plasmonic devices can be very expensive, in some cases costing over US$1500 per device. This high costs prevents these devices from being commercially viable options for characterizing biological materials. Furthermore, without any scope for post-fabrication tuning of the properties of plasmonic device, it is not possible to tailor the optical properties of such plasmonic devices at low cost.

The present invention has been devised in order to address at least one of the above problems. Preferably, the present invention reduces, ameliorates, avoids or overcomes at least one of the above problems.

In a first aspect, the present invention provides a plasmonic device having a base substrate and an electrically conductive film formed on the base substrate, wherein the base substrate has a reference upper surface and an arrangement of chiral nanostructures formed in relief from the reference upper surface, each chiral nanostructure having a nanostructure upper surface which is disposed at a distance of at least 30 nm from the reference upper surface in a thickness direction, wherein the electrically conductive film is formed on the nanostructure upper surface of each chiral nanostructure and on at least part of the reference upper surface of the base substrate.

The plasmonic device of the first aspect of the present invention can be manufactured, for example, using the method of the second aspect of the present invention. Furthermore, as is discussed in detail below, the inventors have found that by altering the thickness of the electrically conductive film, it is possible to fine-tune the optical properties of the plasmonic device at low cost. This represents preferred features of the present invention.

In a second aspect, the present invention provides a method of manufacturing a plasmonic device having a base substrate and an electrically conductive film formed on the base substrate, wherein the base substrate has a reference upper surface and an arrangement of chiral nanostructures formed in relief from the reference upper surface, each chiral nanostructure having a nanostructure upper surface which is disposed at a distance of at least 30 nm from the reference upper surface in a thickness direction, wherein the electrically conductive film is formed on the nanostructure upper surface of each chiral nanostructure and on at least part of the reference upper surface of the base substrate, the method including the steps:

providing the arrangement of chiral nanostructures by moulding of the base substrate; and then forming the electrically conductive film on the nanostructure upper surfaces and the reference upper surface.

Injection moulding is an inexpensive manufacturing technique, capable of high-throughput. The cost of producing a plasmonic device according to the second aspect of the present invention is therefore far lower, and allowing far higher throughput, than the methods used to produce the plasmonic devices of the prior art. This enables the possibility that plasmonic devices of the present invention can be disposable items, intended to be used once and then discarded. This is of particular interest for analysis of biological materials, since the risk of contamination of the device can be reduced if the device is intended to be used only once.

In a third aspect, the present invention provides a method of analysis of at least one biological material, including the steps:

providing a plasmonic device having a base substrate and an electrically conductive film formed on the base substrate, wherein the base substrate has a reference upper surface and an arrangement of chiral nanostructures formed in relief from the reference upper surface, each chiral nanostructure having a nanostructure upper surface which is disposed at a distance of at least 30 nm from the reference upper surface in a thickness direction, wherein the electrically conductive film is formed on the nanostructure upper surface of each chiral nanostructure and on at least part of the reference upper surface of the base substrate;

depositing said at least one biological material onto the plasmonic device;

irradiating the plasmonic device and the biological material with electromagnetic radiation, the arrangement of chiral nanostructures and electrically conductive film thereby generating a superchiral electromagnetic field;

detecting the effect of the presence of the biological material on the superchiral electromagnetic field.

The third aspect may be considered as a method of performing plasmonic polarimetry, using the plasmonic device according to the first aspect.

The method of analysis of the third aspect of the present invention is capable of producing assays with only a very small quantity of biological material, and without the requirement for labels, such as fluorescent labels.

As the skilled person will understand, in the case of a planar plasmonic device the thickness direction is the direction perpendicular to the upper reference surface of the plasmonic device. In the case of a non-planar plasmonic device, the thickness direction is the direction perpendicular to a plane tangential to the upper reference surface of the plasmonic device.

The base substrate may be a polymer material.

The electrically conductive film may be formed on substantially all of the reference upper surface between the chiral nanostructures.

The chiral nanostructures formed in relief may be formed as indentations in the reference upper surface, with the nanostructure upper surface recessed from the reference upper surface. Alternatively, the chiral nanostructures may be formed as protrusions, with the nanostructure upper surface protruding from the reference upper surface. Either approach is feasible using injection moulding.

The chiral nanostructures may have a chiral shuriken shape. Moreover, the chiral nanostructures may have at least one of a left-handed chiral shuriken shape, and a right-handed chiral shuriken shape. The shuriken shapes may have at least 3 arms. Preferably, the shuriken shapes may have at least 4 arms. The inventors have found that shuriken shapes having 6 arms produce desirable results.

The chiral nanostructures may alternatively have a gammadion shape. Moreover, the chiral nanostructures may have at least one of a left-handed gammadion shape, and a right-handed gammadion shape.

Each chiral nanostructure may measure at least 400 nm across (in terms of a straight line distance between the outer peripheral limits of the chiral nanostructure, measured across the centre of the chiral nanostructure). Each chiral nanostructure may measure at most 600 nm across. Moreover, each chiral nanostructure may have an area footprint of at least 0.16 $\mu m^2$. Each chiral nanostructure may have an area footprint of at most 0.36 $\mu m^2$. The inventors have found that chiral nanostructures each having an area footprint of about 0.20 $\mu m^2$ produce desirable effects. The inventors have found that chiral nanostructures of this size produce superchiral electromagnetic fields with sensitivity to the higher-order structure of biological material.

The inventors have found that chiral nanostructures of the size discussed above produce evanescent fields displaying chirality on a suitable length-scale for determining the higher-order structure of proteins.

The nanostructure upper surface may be disposed at a distance of at least 60 nm from the reference upper surface in the thickness direction. The nanostructure upper surface may be disposed at a distance of at most 100 nm from the reference upper surface in the thickness direction. Preferably, the nanostructure upper surface is disposed at a distance of at least 70 nm and more preferably at least 75 nm from the reference upper surface in the thickness direction. Preferably, the nanostructure upper surface is disposed at a distance of at most 90 nm and more preferably at most 85 nm from the reference upper surface in the thickness direction. The inventors have found a distance of about 80 nm to produce desirable effects.

The electrically conductive film may have a substantially uniform thickness. Preferably, the thickness of the electrically conductive film is at least 20 nm. Preferably, the thickness of the electrically conductive film is at most 100 nm.

Side-walls connecting the nanostructure upper surface with the reference upper surface may form an oblique angle with the nanostructure upper surface the reference upper surface. Side-walls connecting the nanostructure upper surface with the reference upper surface may be sloped, forming an angle of between 20° and 40° with the reference upper surface and nanostructure upper surface, respectively. The inventors have found an angle of about 30° to produce desirable effects.

Accordingly, electrically conductive material covers the side-walls, as well as the nanostructure upper surfaces and at least part of the reference upper surface.

The thickness of the electrically conductive film may be less than the distance between the nanostructure upper surface and the reference upper surface.

The thickness of the electrically conductive film may be less than 50% of the distance between the nanostructure upper surface and the reference upper surface.

The thickness of the electrically conductive film may be 50% or more of the distance between the nanostructure upper surface and the reference upper surface.

The thickness of the electrically conductive film may be the same, or about the same, as the distance between the nanostructure upper surface and the reference upper surface.

The thickness of the electrically conductive film may be greater than the distance between the nanostructure upper surface and the reference upper surface.

The arrangement of chiral nanostructures may consist of same-handedness chiral nanostructures.

The chiral nanostructures may be arranged in a square array having a periodicity of between 600 and 800 nm. The inventors have found a periodicity of 700 nm to produce desirable results.

The arrangement of chiral nanostructures may consist of an array of left-handed nanostructures. Alternatively, the arrangement of chiral nanostructures may consist of an array of right-handed nanostructures.

By providing a plasmonic device having an array of left-handed chiral nanostructures, and a plasmonic device having an array of right-handed chiral nanostructures, it is possible to separately measure a value for $\Delta\lambda_L$ and $\Delta\lambda_R$, and accordingly to determine the dissymmetry/asymmetry factor, $\Delta\Delta\lambda$, for biological matter. Therefore, preferably there are provided, as an apparatus, an array of left-handed chiral nanostructures and an array of right-handed chiral nanostructures. For example, a left-handed plasmonic device (having an array of left-handed chiral nanostructures) and a right-handed plasmonic device (having an array of right-handed chiral nanostructures) may be provided on a single plasmonic apparatus.

The plasmonic device may further include a transparent slide overlaid on the electrically conductive film, to form a fluidic cell.

The base substrate may be moulded by an injection moulding step. Moreover, the base substrate may be injection moulded using an injection moulding master copy, the injection moulding master copy having an arrangement of chiral nanostructures formed in relief.

As will be clear to the skilled person, the chiral nanostructures formed in relief in the injection moulding master copy may be a negative of the chiral nanostructures formed in relief from the reference upper surface of the base substrate. In this way, injection moulding using the master copy will produce a base substrate having the structure recited in the first, second and third aspects.

The injection moulding master copy may be a Ni master copy. Alternatively, it may be a Ti master copy. More generally, the injection moulding master copy may be formed of a metallic material. The injection moulding master copy may in turn be formed from a master. The master typically has a shape corresponding to the intended shape of the base substrate. The master may be formed by electron beam lithography, for example. The master copy may be formed by plating over the master.

The electrically conductive film may be formed by evaporating an electrically conductive material onto the base substrate.

The biological material may be a protein.

The method of analysis may further include a step of allowing the biological material to adsorb, or surface-bond, to the plasmonic device.

The step of detecting the effect of the presence of the biological material on the superchiral electromagnetic field may consist of detecting the effect of the presence of the biological material on an electromagnetic field reflected from the surface of the plasmonic device.

Moreover, the step of detecting the effect of the presence of the biological material on the superchiral electromagnetic field may consist of detecting the effect of the presence of the biological material on an ORD spectra of electromagnetic radiation reflected from the surface of the plasmonic device.

The method of analysis may further include a step of detecting the effect of a change in conformation of the biological material on the superchiral electromagnetic field. Such a change in confirmation may occur by introducing a ligand to a protein, for example.

The method of analysis may further including carrying out a multiplex assay, including the steps:

providing an array of said arrangement of chiral nanostructures, to define an array of analysis sites;
depositing a plurality of biological materials, each analysis site respectively receiving a different one of said plurality of biological materials;
irradiating the analysis sites and the biological materials with said electromagnetic radiation;
detecting the effect of the presence of the biological materials on the superchiral electromagnetic field.

In the analysis method steps for carrying out a multiplex assay, each of the analysis sites may be irradiated at the same time, so as to detect the effect of the presence of the biological materials at each of the measurement sites on the superchiral electromagnetic field at the same time.

Alternatively, the analysis sites may be irradiated sequentially, so as to detect the effect of the presence of the biological materials at the measurement sites on the superchiral electromagnetic field sequentially.

Further optional features of the invention are set out below.

BRIEF DESCRIPTION OF THE DRAWINGS

Embodiments of the invention will now be described by way of example with reference to the accompanying drawings in which:

FIG. 2A is a flow-chart showing an exemplary method for manufacturing a plasmonic device according to an embodiment of the present invention.

FIG. 2B is a flow-chart showing an exemplary method for manufacturing a plasmonic device according to an embodiment of the present invention.

DETAILED DESCRIPTION OF THE PREFERRED EMBODIMENTS, AND FURTHER OPTIONAL FEATURES OF THE INVENTION

Figure 1A:
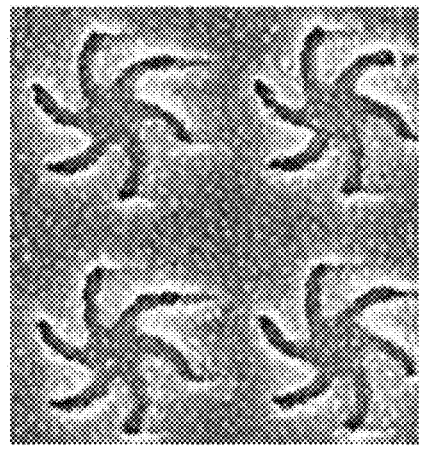
FIG. 1A is an SEM image of a section of a plasmonic device according to an embodiment of the present invention, showing a square array of four right-handed shuriken chiral nanostructures.
Figure 1B:
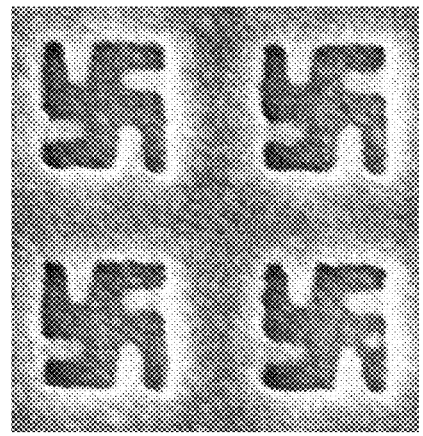
FIG. 1B is an SEM image of a section of a plasmonic device according to an embodiment of the present invention, showing a square array of four right-handed gammadion chiral nanostructures.

FIG. 1A is an SEM image of a section of a plasmonic device, showing a square array of four right-handed chiral nanostructures. FIG. 1B is an SEM image of a section of another plasmonic device, showing a square array of four right-handed chiral nanostructures.

FIG. 2A is a flow-chart showing an exemplary method for manufacturing a plasmonic device, using a Ni master copy. Steps 200-208 of FIG. 2A outline an exemplary process for manufacturing a Ni master copy. Step 210 is an injection moulding step for moulding a base substrate using the Ni master copy. Step 212 is an evaporation step for forming an electrically conductive film on the base substrate. Once steps 200-208 have been performed (i.e. once the Ni master copy has been made), steps 210 and 212 can be repeated without the requirement to make another master copy. If the master copy wears out, further master copies can be made. Accordingly, the relatively expensive and time-consuming step of patterning a master with chiral nanostructures only has to be performed once. Multiple plasmonic devices comprising a base substrate and an electrically conductive film can therefore be manufactured with relative ease. By automating steps 210 and 212 using a single Ni master copy, high-throughput production of plasmonic devices can be achieved, with the unit cost of each plasmonic device being low. In effect, injection moulding and evaporation can be used to manufacture low-cost, disposable plasmonic devices.

In step 200, a poly(methyl methacrylate) (PMMA) electron beam (e-beam) resist is spin-coated onto the Si substrate. This resist is oven baked at 180° C. for 1 hr, in order to evaporate the solvent from the PMMA. As will become clear below, the thickness of the PMMA resist layer on the Si substrate defines a distance from a reference upper surface of the base substrate, to a nanostructure upper surface of the base substrate. That is, the thickness of the PMMA layer defines the depth of the chiral nanostructures. The thickness of the PMMA layer may be 80 nm. In step 202, the PMMA resist layer is patterned with an arrangement of chiral nanostructures using an e-beam. In step 204, the patterned PMMA is developed in a solution of iso-propanol (IPA) and methyl isobutyl ketone (MIBK) for 60 seconds, so as to remove the PMMA regions that have been exposed to the e-beam. Development time will vary depending on PMMA film thickness, and on the particular arrangement of chiral nanostructures. After development, PMMA chiral nanostructures remain in relief from the upper surface of the Si substrate, with the depth of the chiral nanostructures being equal to the thickness of the PMMA layer. In step 206, a layer of Ni is electrodeposited onto the surface of the Si substrate. The thickness of the electrodeposited Ni may be 1 mm. In step 208, lift-off is performed in acetone, thereby removing the PMMA resist and liberating the Ni layer from the Si substrate. A Ni master copy is thereby produced, with the chiral nanostructures of the PMMA transferred to the surface of the Ni master copy. Hence, a Ni master copy having an arrangement of chiral nanostructures formed in relief, is produced.

In step 210, the Ni master copy is used as an injection mould for injection moulding a polymer base substrate. The arrangement of chiral nanostructures of the Ni master copy are thereby transferred to the injection moulded polymer, producing a base substrate with an arrangement of chiral nanostructures formed in relief from an upper reference surface. The distance from a reference surface of the base substrate to a nanostructure upper surface of the base substrate in the thickness direction, is equal to the thickness of the PMMA layer formed in step 200.

In step 212, an electrically conductive material is evaporated onto the upper surfaces of the base substrate, to form an electrically conductive film on the base substrate. By carefully controlling the evaporation of the electrically conductive material, an electrically conductive film of uniform thickness can be formed on the reference upper surface and nanostructure upper surfaces of the base substrate. The electrically conductive film will therefore take the shape of the chiral nanostructures formed in relief from the reference upper surface of the base substrate. In exemplary embodiments, side-walls of the polymer base substrate may be sloped, forming an oblique angle with the reference upper surface and nanostructure upper surfaces. This slope enables the polymer base substrate to be easily liberated from the master copy. Advantageously, the slope also enables electrically conductive material evaporated onto the base substrate to coat the side-walls, forming an electrical connection between the electrically conductive film covering the reference upper surface, and the electrically conductive film covering the nanostructure upper surfaces. Hence, the electrically conductive layer is continuous.

The resulting base substrate and electrically conductive film collectively form a plasmonic device. As discussed in detail below, the thickness of the electrically conductive film can be controlled, in order to control the optical properties of the plasmonic device.

FIG. 2B is a flow-chart showing another exemplary method for manufacturing a plasmonic device, using injection moulding with a non-magnetic (non-ferrous) master copy. The injection moulding and evaporation steps of FIG. 2B (steps 230 and 232) correspond to the injection moulding and evaporation steps of FIG. 2A (steps 210 and 212), but with a non-ferrous master copy used. As with the example of FIG. 2A, the non-ferrous master copy can be reused in order to create low-cost, disposable plasmonic devices.

In the method of FIG. 2B, Ti (a non-ferrous metal) is used as the initial substrate. The metal substrate used is a Ti substrate (or brass) in particular due to its excellent thermal properties and strength. In step 214, the Ti substrate is polished to roughly <50 nm surface roughness. It is then cleaned with an alkaline based solvent and rinsed with acetone, methanol and IPA. In step 216, the Ti substrate is then spin coated with SU-8 3005 photoresist. This photoresist will further reduce surface roughness. It will also create a passivating layer, reducing any oxidation of the Ti surface and nullify any roughness resulting from any oxidation of the Ti surface that may take place during any subsequent heating or baking steps. The photo resist is baked at 90° C. on a hotplate for 1 hour which will evaporate any solvent and create a smooth and flat surface. The photoresist is exposed to light that will cross link the resist. The substrate is then baked on a hot plate 90° C. for a further 5 mins to complete the cross linking step and harden the resist. In step 218, a metal film (100 nm Al in our case) is deposited onto the surface of the substrate. This metal film will act as a charge conduction layer for the e-beam step, as the photoresist in an insulator. The metal film will also improve surface adhesion for the metal deposition that will define the chiral nanostructures of the master and improve the substrates ability to withstand adhesion to hot injected polymer in the injection moulding step, else the polymer and the photoresist which is also a polymer, will have strong adhesion and the photoresist will rip apart in the injection moulding step. Step 220 corresponds to step 200. Step 222 corresponds to step 202, step 224 corresponds to step 204. In step 226, a metal layer is deposited on the surface of the substrate (on the patterned PMMA), where the layer thickness is always less than ⅔ of the PMMA thickness. The metal layer consists of an adhesion layer (Ti with a thickness of 5 nm in our case) and another soft metal (Au in our case) for the rest of the layer to help with the lift-off process in step 228). The total metal thickness in this case will define the depth of the nanostructures/recession/indentation in the final injection moulded base substrate. In step 228, lift-off of the excess metal and PMMA is performed using acetone. Once the lift-off has occurred, the master copy is complete and can be used for the injection moulding steps, 230-232.

Figure 3A:
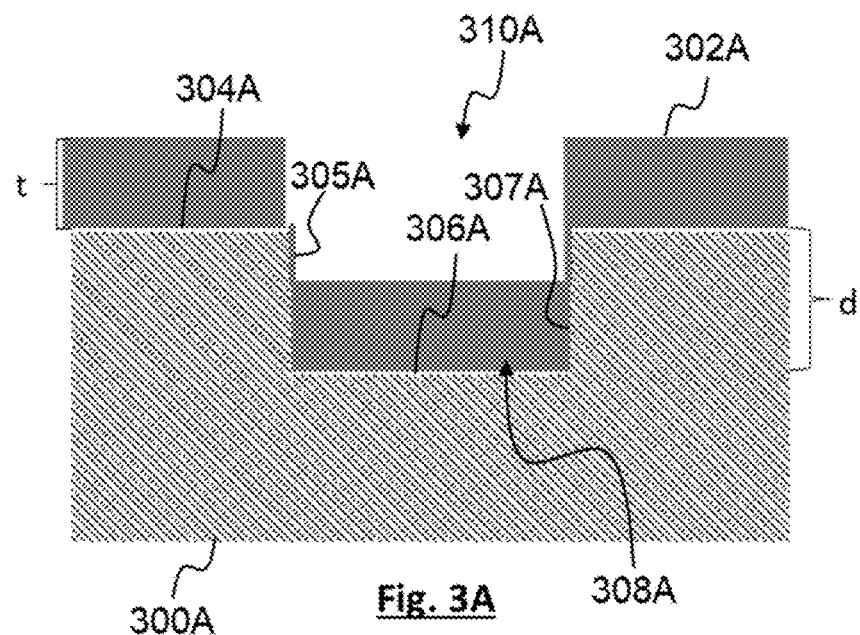
FIG. 3A shows a simplified cross-sectional view of a base substrate and electrically conductive film for use in an embodiment of the present invention.

FIG. 3A shows a simplified cross-sectional view of a base substrate 300A with an electrically conductive film 302A formed on it. The base substrate has a single chiral nanostructure formed as an indentation in a reference upper surface 304A, the chiral nanostructure having a nanostructure upper surface 306A disposed at a distance, d, from the reference upper surface 304A in the thickness direction. Side walls 307A connect the nanostructure upper surface with the reference upper surface. In practice, the side walls 307A slope inwards, forming a non-zero angle with the thickness direction. Electrically conductive material 305A coats the side-walls, forming an electrical connection between the electrically conductive material formed on the reference upper surface 304A, and the electrically conductive material formed on the nanostructure upper surfaces, 306A. The electrically conductive film has a uniform thickness t. As is discussed in detail below, the thickness t as a proportion of the distance d, can be controlled in order to adjust the optical characteristic of the plasmonic device. The electrically conductive film will take the shape of the chiral nanostructures formed in relief from the reference upper surface of the base substrate. In other words, a depth of the chiral nanostructures formed in the electrically conductive film will be equal to the distance, d.

Figure 4A:
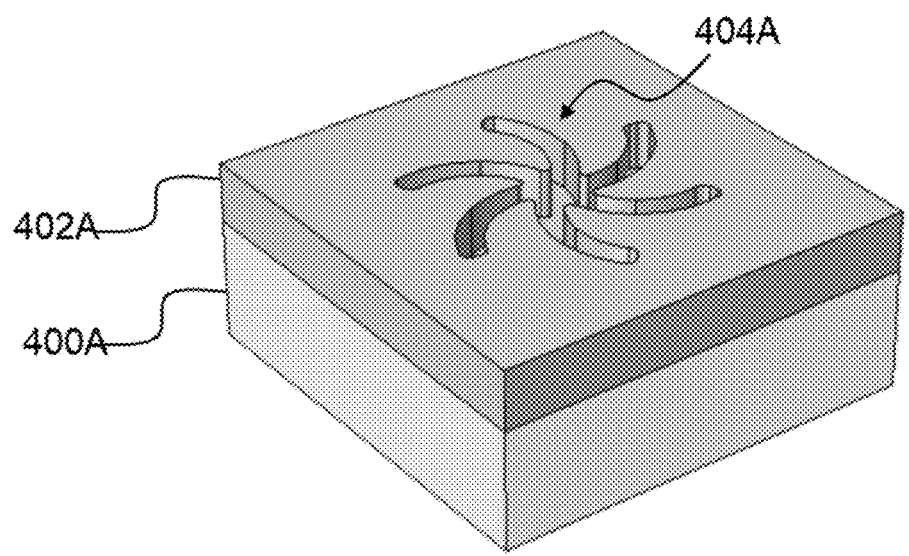
FIG. 4A shows a schematic perspective view of a chiral nanostructure for use with a preferred embodiment of the present invention.

FIG. 4A shows a perspective view of a base substrate 400A and electrically conductive film 402A, with a single chiral nanostructure 404A formed in relief. As can be seen from FIG. 4A, the chiral nanostructure is formed as a recess.

Figure 3B:
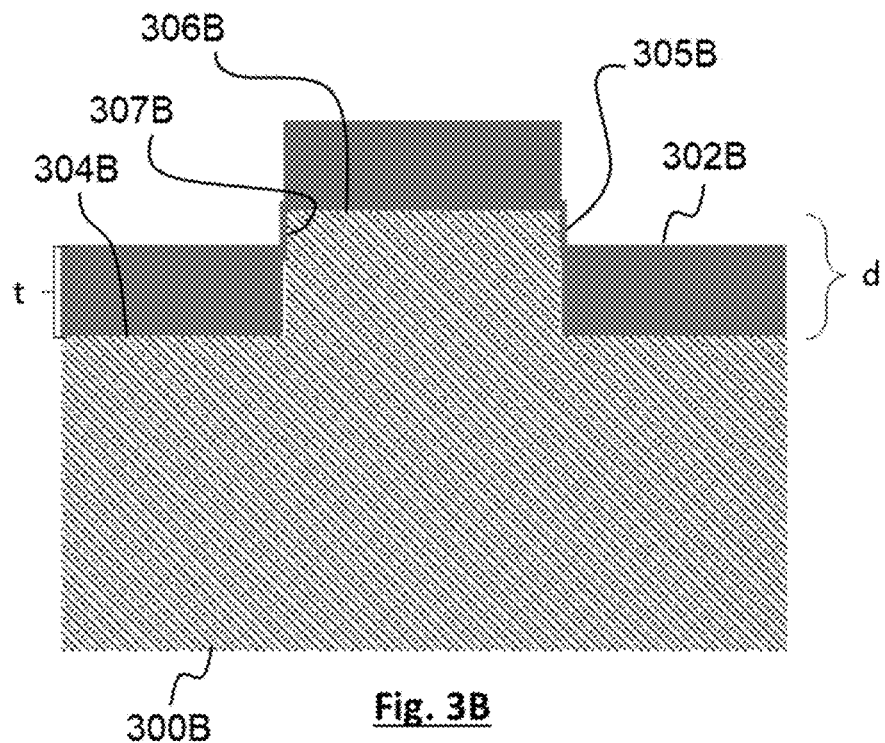
FIG. 3B shows a simplified cross-sectional view of a base substrate and electrically conductive film for use in another embodiment of the present invention.

FIG. 3B shows a simplified cross-sectional view of a further embodiment in which a base substrate 300B has an electrically conductive film 302B formed on it. The base substrate has a single chiral nanostructure formed as a protrusion from a reference upper surface 304B, the chiral nanostructure having a nanostructure upper surface 306B disposed at a distance, d, from the reference upper surface 304A in the thickness direction. Side walls 307B connect the nanostructure upper surface with the reference upper surface. In practice, the side walls 307B slope inwards, forming a non-zero angle with the thickness direction. Electrically conductive material 305B coats the side-walls, forming an electrical connection between the electrically conductive material formed on the reference upper surface 304B, and the electrically conductive material formed on the nanostructure upper surfaces, 306B. The electrically conductive film has a uniform thickness t. As is discussed in detail below, the thickness t as a proportion of the distance d, can be controlled in order to adjust the optical characteristic of the plasmonic device. The electrically conductive film will take the shape of the chiral nanostructures formed in relief from the reference upper surface of the base substrate. In other words, a depth of the chiral nanostructures formed in the electrically conductive film will be equal to the distance, d.

Figure 4B:
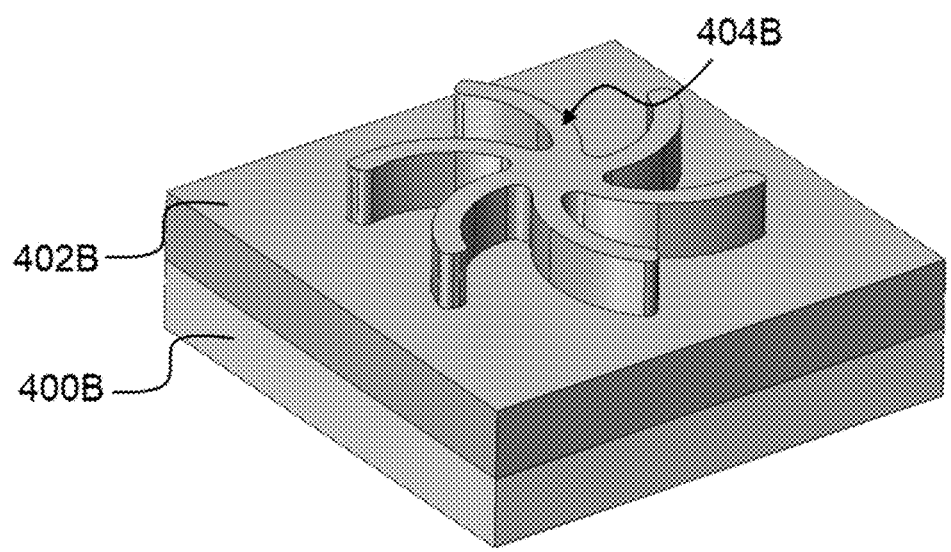
FIG. 4B shows a schematic perspective view of a chiral nanostructure for use with another preferred embodiment of the present invention.

FIG. 4B shows a perspective view of a base substrate 400B and electrically conductive film 402B, with a single chiral nanostructure 404B formed in relief. As can be seen from FIG. 4B, the chiral nanostructure is formed as a protrusion.

Typically, the above method of manufacture is used to produce plasmonic devices consisting of arrays of chiral nanostructures. Example arrays of chiral nanostructures are shown in FIGS. 1a and 1b. Moreover, in exemplary embodiments of the present invention, plasmonic devices may consist of an array of same-handedness chiral nanostructures. For example, the above method may be used to manufacture left-handed plasmonic devices consisting of an array of left-handed chiral nanostructures, and right-handed plasmonic devices, consisting of an array of right-handed chiral nanostructures.

As will become clear from the following discussion, such left and right-handed plasmonic devices are useful for performing plasmonic polarimetry analysis.

Optical Properties of Injection Moulded Plasmonic Devices

As shown in FIGS. 3A and 4A, the manufacturing method results in plasmonic devices in which the chiral nanostructures are formed in relief. Moreover, in FIGS. 3A and 4A, the chiral nanostructures are formed as recesses. Each nanostructure feature consists of an electrically conductive solid nanostructure 308A (the part of the recess filled with electrically conductive material), and an identically shaped nanostructure void/inverse nanostructure 310A, directly above the solid nanostructure. In the following discussion, this configuration is referred to as a solid-inverse structure.

In line with Babinet's principle, the roles of electric and magnetic fields are switched between the solid and inverse structures. Without wishing to be bound by theory, it is thought that the implications of this are that symmetry equivalent electric and magnetic modes of the solid and inverse nanostructures are spatially located directly above each other, and can consequently couple in an analogous manner to hybridization of orbitals in molecular systems. By controlling the spatial overlap between the solid and inverse structure, through electrically conductive film thickness t, the coupling between electric and magnetic modes can be controlled, thus enabling the optical properties of the plasmonic device to be manipulated with relative ease. Hence, optical properties of the plasmonic devices can be manipulated with a single geometric design, e.g. with a single injection moulding master copy.

Figure 5:
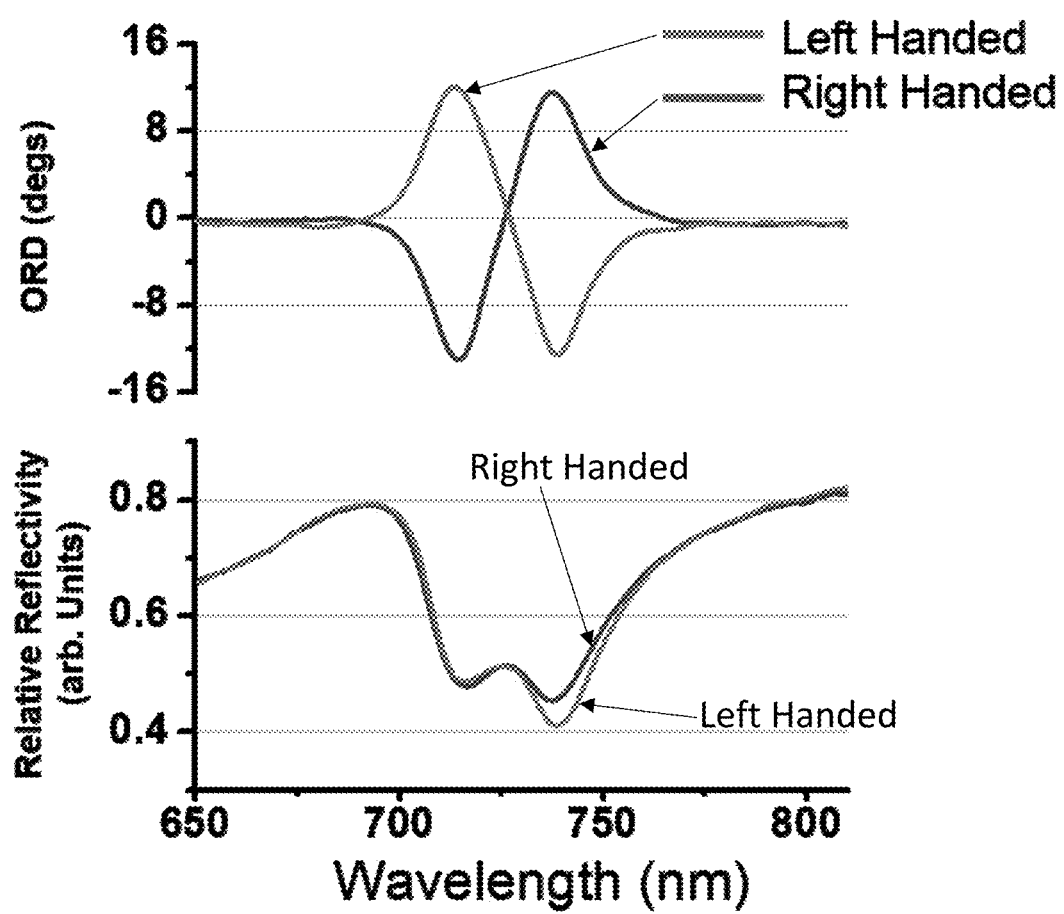
FIG. 5 shows ORD spectra (top) and reflectivity spectra (bottom) as a function of wavelength, for electromagnetic radiation reflected from a left-handed plasmonic device, and from right-handed plasmonic device, without any chiral material deposited onto either device.

FIG. 5 shows ORD and reflectivity spectra for electromagnetic radiation reflected from a left-handed plasmonic device, and from right-handed plasmonic device, without any chiral material deposited onto either device. FIG. 5 clearly shows that the ORD spectrum (top graph) for the left-handed array is the mirror-image of the ORD spectrum from the right-handed array, in the electromagnetic wavelength region from 700 nm to 770 nm. Hence, the ORD spectra confirm that the left and right-handed plasmonic devices do indeed have chiral optical properties. As is also clear from FIG. 5, reflectivity is independent of handedness. Minor differences between the left-handed and right-handed spectra of FIG. 5 can be attributed to minor variations in the level of defects, rather than underlying optical effects resulting from the chiral nanostructures themselves.

Figure 6:
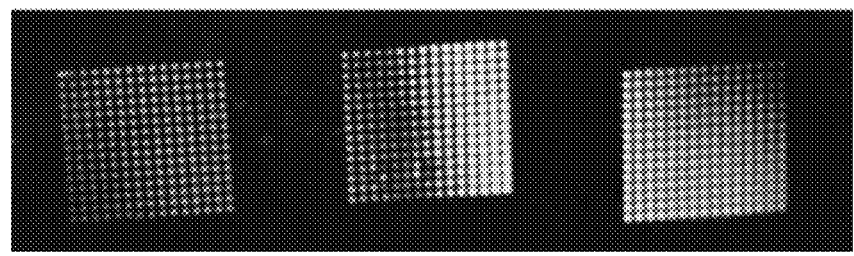
FIG. 6 shows an image of a slide with 675 chiral and achiral nanostructures formed in it, split into three nanostructure arrays, each array having 225 nanostructures.

FIG. 6 shows 657 nanostructures (some left-handed chiral, some right-handed chiral, and some achiral) on a single slide. The nanostructures of FIG. 6 are split into three nanostructure arrays, each array containing 225 (15×15) nanostructures. The nanostructures on the slide of FIG. 6 are gammadions, although this is not visible in FIG. 6. In the original image (not shown), the colour of the left side group of nanostructures is purple, the colour of the middle group of nanostructures is green and the colour of the right side group of nanostructures is orange.

Below, the effect of the thickness of the electrically conductive film on the optical properties of plasmonic device, is investigated. Left-handed and right-handed plasmonic devices were fabricated as described above.

For the purpose of the following discussion, the base substrate was formed by injection moulding a polycarbonate base substrate using a Ni master copy. Au was used as the material for the electrically conductive film. The chiral nanostructures were shuriken nanostructures with 6 arms. The depth of the chiral nanostructure features (i.e. the distance from the reference upper surface of the base substrate to the nanostructure upper surfaces of the base substrate in the thickness direction) was 80 nm, with the side-walls of each chiral nanostructure sloping inwards to form an angle of approximately 30° with the thickness direction. Au coated the side-walls of the chiral nanostructures, thereby forming a continuous electrically conductive film. The inventors have found that a continuous electrically conductive layer is essential for the desired optical properties to be achieved. The edges of the chiral nanostructures were slightly rounded. The area footprint of each chiral nanostructure was 0.20 µm². The chiral nanostructures were arranged in a square lattice array, with a lattice constant of 700 nm. The Au layer was formed with a range of thicknesses, from 20 nm to 100 nm.

Figure 7:
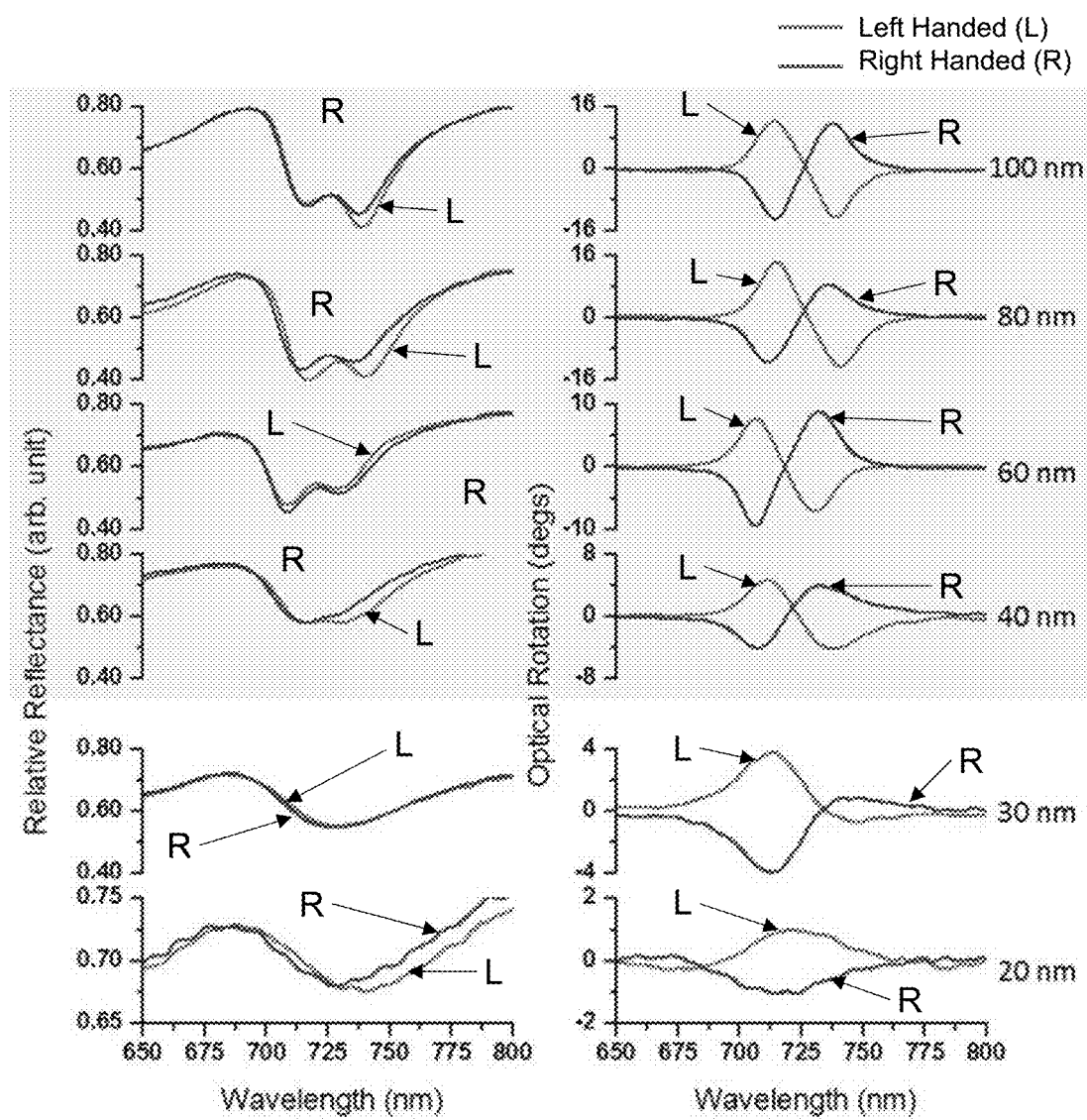
FIG. 7 shows graphs of reflectance spectra (left-hand column), and ORD spectra (right-hand column), as a function of wavelength, for left and right-handed plasmonic devices having electrically conductive film thicknesses of 20 nm, 30 nm, 40 nm, 60 nm, 80 nm and 100 nm, without any deposited chiral material.

ORD spectra of left and right-handed plasmonic devices, immersed in a buffer solution of Trizma® hydrochloride (Tris-HCl), as a function of Au film thickness, are shown in FIG. 7.

FIG. 7 shows graphs of reflectance spectra as a function of wavelength (left-hand column), and ORD spectra as a function of wavelength (right-hand column), for left and right-handed plasmonic devices.

The relative reflectance of FIG. 7 was calculated relative to an unpatterned (i.e. flat planar) Au film of the same thickness. ORD and rotation spectra are shown for plasmonic devices with film thicknesses of 20 nm, 30 nm, 40 nm, 60 nm, 80 nm and 100 nm. ORD measurements were made by irradiating the plasmonic devices with linearly polarized electromagnetic radiation, with a polarization direction parallel to the plane of the plasmonic devices, and measuring the optical rotation of the reflected light as a function of wavelength.

As is clearly illustrated in FIG. 7, the ORD and reflectivity spectra are strongly dependent on film thickness.

Broadly speaking, the ORD spectra shown in FIG. 7 can be split into two groups, based on the observed ORD spectra and reflectance spectra. That is, they can be split into: a first group in which the thickness, t, of the electrically conductive film is 50% or more of the distance, d, between the reference upper surface and the nanostructure upper surface; and a second group, in which the thickness, t, of the electrically conductive film is less than 50% of the distance, d, between the reference upper surface and the nanostructure upper surface.

The chiral arrays having an Au thickness of 40 nm or more (50% of the distance d or more) are clearly shown as having a higher chirality. Chiral arrays having an Au thickness of 40 nm or more are therefore particularly suitable for determining the structure of proteins using dissymmetry/asymmetry factors.

A theoretical discussion of the dependence of chirality on electrically conductive film thickness is set out below. As discussed below, the higher chirality seen in the thicker Au films is attributable to an increased spatial overlap, and increased hybridization, between the solid and inverse nanostructures. This overlap is proportional to the thickness of the electrically conductive layer.

FIG. 8A shows experimental ORD spectra for a left-handed plasmonic device array with a film thickness of 100 nm. FIG. 8B shows simulated ORD spectra for a left-hand plasmonic device with a film thickness of 100 nm. FIG. 8C shows experimental ORD spectra for a left-handed chiral array having a film thickness of 30 nm. FIG. 8D shows simulated ORD spectra for a left-handed chiral nanostructure array having a film thickness of 30 nm.

FIGS. 8E-8J show surface plots of the z-component of E-field density with the polarization of the incident EM radiation parallel to the direction of the arrow of FIG. 8E. The units of the E-field values in the bar to the right of FIGS. 8E-8H are in units of $MVm^{-1}$. FIG. 8E shows a surface plot at the top surface of the 100 nm Au film. FIG. 8F shows a surface plot at the bottom surface of the 100 nm Au film. FIG. 8G shows a surface plot at the top surface of the 30 nm Au film. FIG. 8G shows a surface plot at the bottom surface of the 30 nm Au film. FIG. 8I and FIG. 8J show a cross-sectional view of the z-component of the E-field density through a single chiral nanostructure having a 100 nm Au film and 30 nm Au film respectively. The dashed lines of FIGS. 8I and 8J show the positions of the top surface and bottom surface of a single chiral nanostructure having a 100 nm Au film, and a single chiral nanostructure having a 30 nm Au film, respectively.

The thickness dependency of the ORD spectra is qualitatively reproduced by EM modelling, as shown in FIGS. 8A-8D, with a slight blue shift, attributed to rounding of edges and inhomogeneity in experimental samples. The E-field surface plots shown in FIGS. 8E-J show strong field enhancements at the edges of the chiral nanostructure as well as surface plasmon polaritons (SPP) generated by the structures on the surface of the film. [27,28]

The changes in optical properties can all be understood in terms of the increasing strength of the coupling between electric and magnetic modes as the spatial overlap of the solid and inverse structures increases with film thickness. In the subsequent discussion the approach of Hentshel et al

[24] is used to visualize the coupling of magnetic and electric modes within a solid-inverse structure solely in terms of electric fields.

The dips observed in reflectance spectra collected for Au films of nominal thickness ≤30 nm have a characteristic asymmetric line shape of a Fano resonance [29,30], which in plasmonic systems arises through coupling between a "continuum state", a broad optically bright mode, and a "discrete state", a narrow dark mode [31]. EM modelling of the electric and magnetic field in the vicinity of the 30 nm film, FIGS. 8G and 8H, show different spatial distributions on the top and bottom surfaces. Overlap between the electric and magnetic fields of the top and bottom surface are not maximized, thus coupling between the inverse and solid structures is not optimal. It should be noted that due to its reduced thickness, the SPP propagate on both sides of the 30 nm film and evanescent fields are visible in the dielectric surrounding the solid structure and are to be ignored for this discussion [32,33]. As the thickness is increased further (40 nm), a significant change in the reflectance dip occurs. A peak of enhanced reflectivity begins to develop within the dip, becoming more pronounced with increasing film thickness. Peaks of enhanced reflectivity within reflectance dips have been observed previously in solid-inverse plasmonic structures [24]; attributed to an electromagnetically induced transmission (EIT) like phenomena. The origin of this EIT-like effect is due to strong coupling between bright and dark modes of the solid-inverse structure. For the 100 nm structure, FIGS. 8E and 8F, the electric fields associated with the top and bottom surface have matching spatial distributions but are out of phase; while the corresponding magnetic fields also have identical distributions and are in-phase, indicative of optimal coupling.

Figure 9:
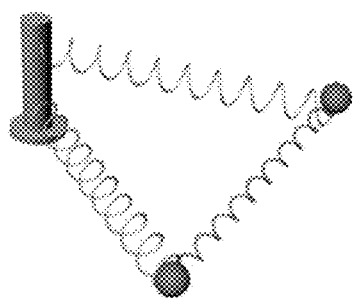
FIG. 9 shows an illustration of dynamic coupling according to the Born-Kuhn model.
Figure 10:
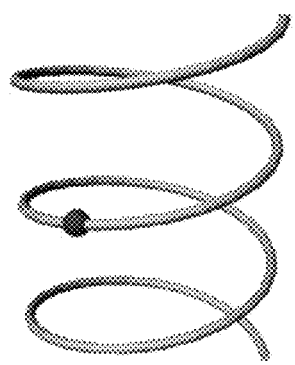
FIG. 10 shows an illustration of a simple helical oscillator (SHO).

In the case of the chiral structures disclosed herein, the film thickness dependence of the coupling behaviour has implications that extend beyond reflectivity characteristics. Significant changes in ORD spectra occur concurrently with those observed in reflectance. Further analysis of this behaviour provides an insight into how the coupling between the two solid and inverse nanostructures alters with increasing film thickness, and how this changes the nature of the chirality. Using the analogy of natural optical activity occurring in molecules, it is useful to classify chromophores showing natural optical activity in terms of two limiting types [34]: the inherently chiral chromophore in which the electronic states are delocalized over a chiral nuclear framework so that parallel components of electric and magnetic dipole moments are fully allowed for all transitions and which may be pictured as a single helical oscillator (SHO); and the inherently achiral chromophore where coupling with the chiral environment is required. Two distinct coupling mechanisms can be distinguished [35]. The 'static coupling' mechanism invokes mixing of the electric and magnetic dipole transition moments on the same inherently achiral chromophore due to perturbations from the electrostatic fields of other groups in its chiral environment; and the 'dynamic coupling' or 'coupled oscillator' mechanism where the perturbations are due to electrodynamic fields radiated by other groups under the influence of electromagnetic radiation and which becomes an 'exciton' model in the case of degenerate transitions on two identical chromophores. ORD spectra from chiral nanostructure arrays of 20 and 30 nm nominal Au thicknesses display the characteristic line shape associated with dynamic coupling [35] and might be described by a plasmonic realization of the Born-Kuhn model shown in FIG. 9; whereas those from film thicknesses of ≥40 nm display the line shape associated with static coupling [35] (FIG. 10) which is also expected for an inherently chiral chromophore (SHO), the latter being more likely due to the large increase in the corresponding ORD signal, a typical property of inherently chiral chromophores. This difference in line shape implies that with increasing film thickness, there is a switch from an interaction between two or more dynamically coupled electric dipole transition moments to an interaction between spatially overlapping electric and magnetic dipole transition moments.

The film thickness dependency of the optical properties of the chiral nanostructure arrays can be understood in terms of increasing hybridization between magnetic and electric modes, with spatial overlap between the two. To provide a qualitative understanding of the coupling between the electric and magnetic modes of the solid and inverse structures a hybridisation scheme, analogous to a molecular orbital diagram, can be constructed. This is shown in FIG. 11 [23,37].

Figure 11:
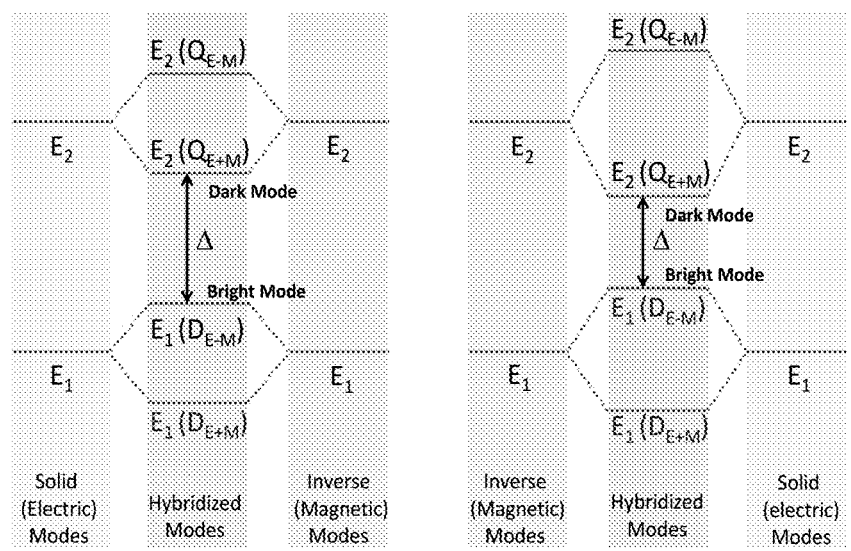
FIG. 11 shows molecular orbital diagrams for thin films with low spatial overlap (left-hand column) and for thin films with larger spatial overlap (right-hand column).

On the left in FIG. 11 is a molecular orbital diagram for thin films with lower spatial overlap. On the right in FIG. 11 is a molecular orbital diagram for thick films with larger spatial overlap.

As with molecular orbital diagrams, the first step in developing a hybridization scheme is to perform a symmetry analysis of the electric and magnetic modes of the solid and inverse structures. The chiral nanostructures considered in FIG. 8 belong to the C6 point group, hence the electric modes of the solid structure, and the symmetry identical magnetic modes of the inverse structure, belong to A, B, E1 and E2 symmetries. Symmetry arguments are based on the information in Table 1, below.

TABLE 1

| $C_6$ | E | $C_6$ | $C_3$ | $C_2$ | $(C_3)^2$ | $(C_6)^5$ | linear functions, rotations | Quadratic functions |
|---|---|---|---|---|---|---|---|---|
| A | 1 | 1 | 1 | 1 | 1 | 1 | $z, R_z$ | $x^2 + y^2, z^2$ |
| B | 1 | −1 | 1 | −1 | 1 | −1 | — | — |
| $E_1$ | 1 | +ε | −ε* | −1 | −ε | +ε* | $x + iy$; $R_x + iR_y$ | (xz, yz) |
|  | 1 | +ε* | −ε | −1 | −ε* | +ε | $x − iy$; $R_x − iR_y$ |  |
| $E_2$ | 1 | −ε* | −ε | +1 | −ε* | −ε | — | $(x^2 − y^2, xy)$ |
|  | 1 | −ε | −ε* | +1 | −ε | −ε* |  |  |

Figure 12A:
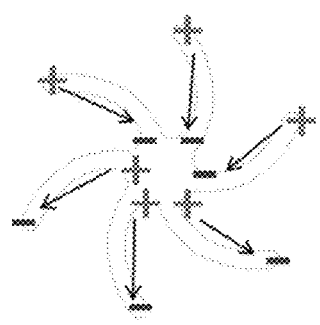
FIG. 12A shows an E1 type symmetry mode.
Figure 12B:
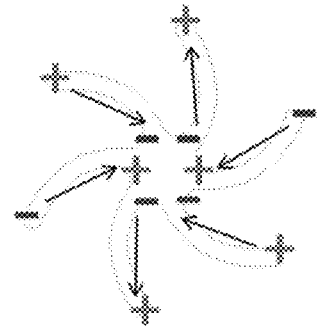
FIG. 12B shows an E2 type symmetry mode.

FIG. 12A shows the E1 type symmetry mode. FIG. 12B shows the E2 type symmetry mode.

Figure 8:
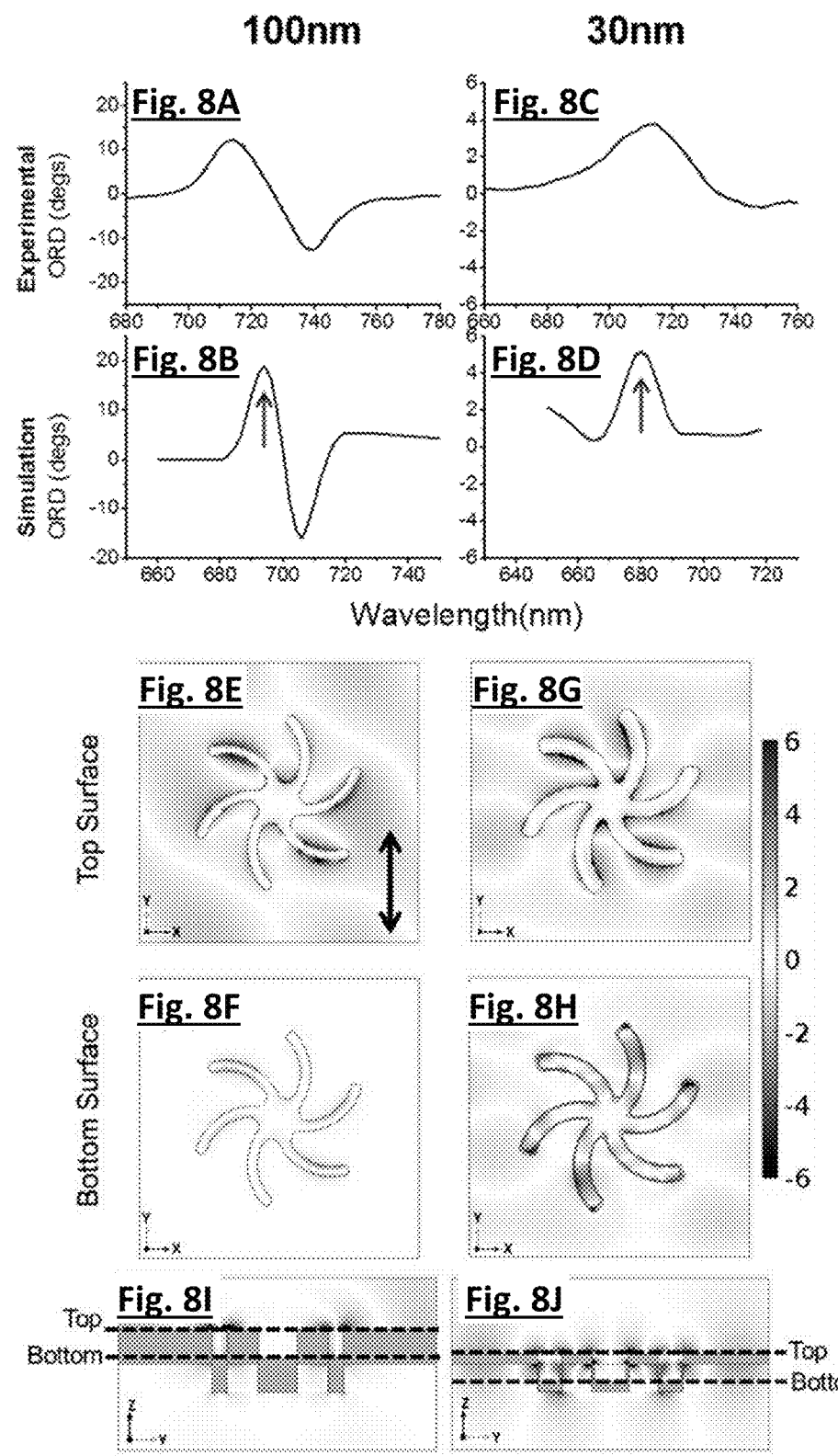
FIG. 8A shows experimental ORD spectra as a function of wavelength, for a left-handed plasmonic device array with a film thickness of 100 nm.
FIG. 8B shows simulated ORD spectra as a function of wavelength, for a left-hand plasmonic device with a film thickness of 100 nm.
FIG. 8C shows experimental ORD spectra as a function of wavelength, for a left-handed chiral array having a film thickness of 30 nm.
FIG. 8D shows simulated ORD spectra as a function of wavelength, for a left-handed chiral nanostructure array having a film thickness of 30 nm.
FIG. 8E shows a computational top-surface plot of the z-component of E-field density for a plasmonic device with a film thickness of 100 nm.
FIG. 8F shows a computational bottom-surface plot of the z-component of E-field density for a plasmonic device with a film thickness of 100 nm.
FIG. 8G shows a computational top-surface plot of the z-component of E-field density for a plasmonic device with a film thickness of 30 nm.
FIG. 8H shows a computational bottom-surface plot of the z-component of E-field density for a plasmonic device with a film thickness of 30 nm.
FIG. 8I shows a computational cross-sectional plot of the z-component of E-field density for a plasmonic device with a film thickness of 100 nm Au film.
FIG. 8J shows a computational cross-sectional plot of the z-component of E-field density for a plasmonic device with a film thickness of 30 nm Au film.

Modes with A and E1 symmetry are optically bright since they have dipolar character; but only the E1 mode is accessible in the normal incident experimental geometry used, since the A mode can only be excited by vertical components of the exciting field ($E_z$ or $B_z$). The EM modelling shown in FIGS. 8E to 8H reiterates the excitation of an E1 mode as the E fields of both structures show an inversion in polarity for a C2 rotation (see Table 1 and FIG. 12A). The lowest energy dark mode is the E2 mode which has a quadrupolar character; the B mode is also dark but is a higher order multipole and will have a higher energy. Since they have equivalent symmetry the electric dipole (quadrupole) and magnetic dipole (quadrupole) modes of the solid and inverse structures can hybridize. This produces new hybridization, which using the labelling of molecular orbitals, can be referred to as in- and out-of-phase modes, the former having the lowest energy. The in-phase out-of-phase combinations for the dipole solid-inverse modes are labelled $D_{E+M}$ and $D_{E−M}$ respectively; while for the solid-inverse quadrupole modes they are $Q_{E+M}$ and $Q_{E-M}$. The level of hybridization, and hence splitting of the in and out-of-phase modes, increases with spatial overlap. Since the dipole-dipole and quadrupole-quadrupole interactions have $r^3$ and $r^5$ dependencies, increasing spatial overlap will cause a larger splitting of the $Q_{E-M}$ and $Q_{E+M}$ than the $D_{E-M}$ and $D_{E+M}$ levels, shown in FIG. 11. The ORD and reflectivity peaks observed in FIGS. 7 and 8 are associated with the out-of-phase $D_{E-M}$ "bright" mode. This assignment is consistent as the EM modelling in FIGS. 8E to 8H, which show anti-phase electric field patterns observed on the upper and lower surface for an excitable mode that correspond to an E1 symmetry. The optical properties of the substrate could be influenced by the periodic arrangement of chiral nanostructures. A square lattice belongs to the C4 point group, but the presence of chiral nanostructures reduces the symmetry of the extended lattice to C2. In a C2 point group, all modes of the structure would be dipole active (bright) and consequently a Fano resonance would not be possible. Our observations suggest that in the structures of FIGS. 8E to 8H, the lattice symmetry does not significantly influence the chiroptical properties, which are solely governed by symmetry of the chiral nanostructures.

The change from the Born-Kuhn to SHO chirality is inherent in the hybridization model, as greater spatial overlap implies larger level of mixing of the magnetic and electric modes. The transition to EIT behaviour, and thus the implicit increase in overlap between bright and dark modes, can also be understood in terms of the hybridization scheme. The energy separation, $\Delta$, between the bright ($D_{E-M}$) and the dark ($Q_{E+M}$) modes decreases with increasing spatial overlap, thus resulting in greater coupling.

Multiplexing

Figure 13A:
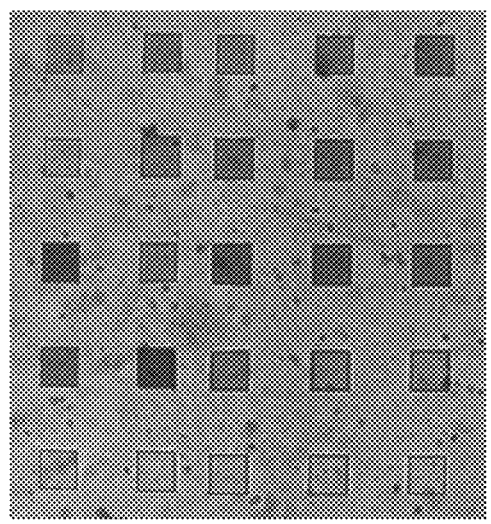
FIG. 13A shows a plasmonic apparatus, consisting of a 5×5 array of plasmonic devices.

It is possible to provide a plasmonic apparatus having an array of discrete analysis sites. For example, a plasmonic apparatus can be provided with an array of discrete plasmonic devices, each plasmonic device consisting of an array of same-handedness chiral nanostructures, and each thereby providing a single analysis site. FIG. 13A shows an exemplary 5×5 array of 25 discrete plasmonic devices. With this device, it is possible to irradiate each of the analysis sites in a single measurement run, thereby obtaining ORD spectra for each measurement site. By placing different proteins at each measurement site, for example, it is therefore possible to obtain ORD spectra for the different proteins in a single measurement run, in order to determine the structure of different proteins in a single measurement run. Hence, a multiplex assay can be performed in this way.

The analysis sites of the plasmonic apparatus can be irradiated at the same time. Then, using imaging techniques can be used to analyse the ORD spectra from each analysis site from a single 'image'. In particular, the plasmonic apparatus is irradiated (i.e. all of the analysis sites are irradiated) with monochromatic light at a fixed polarization, and the reflected/transmitted light intensity is measured at four different polarization directions relative to the input polarization direction, using a polarizer/analyser. This is repeated for incrementally increasing wavelengths, in order to obtain ORD spectra for the desired wavelength range, according to Stokes' method. Alternatively, the entire apparatus is irradiated across the desired wavelength range with light of a fixed polarization direction, and the reflected/transmitted spectra is measured for four different polarization directions relative to the input polarization direction, using a polarizer/analyser, in order to obtain ORD spectra according to Stokes' method. This measurement technique produces a dataset of pixels, each pixel having its own ORD spectral values. Imaging techniques can then be used to resolve the ORD spectra from each analysis site, thereby producing an ORD spectra for each measurement site (and each corresponding protein) at the same time.

Alternatively, each of the analysis sites may be irradiated sequentially, so as to detect the effect of the presence of the biological materials at each of the measurement sites on the superchiral electromagnetic field sequentially. In particular, digital micro mirror devices can be used to individually scan each analysis site onto a spectrometer, to create a complex data set for each analysis site. In this way, ORD spectra for each analysis site, and each corresponding protein, can be obtained.

Figure 13B:
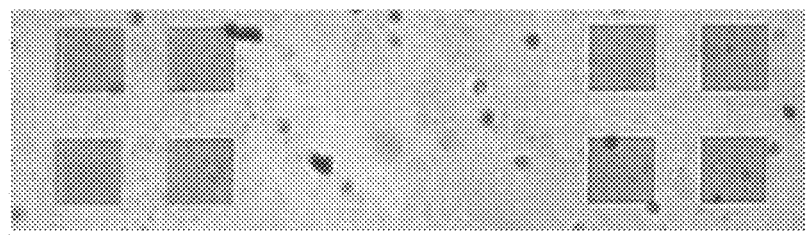
FIG. 13B shows a plasmonic apparatus, consisting of a 2×2 array of left-handed photonic devices (left-hand side of the image) and a 2×2 array of right-handed photonic devices (right-hand side of the image).

FIG. 13B shows a plasmonic apparatus including a 2×2 array of left-handed plasmonic devices (each having an array of left-handed chiral nanostructures) on the left, and a 2×2 array of right-handed plasmonic devices on the right. By a different protein on each of the four left-handed plasmonic devices, and placing the same four proteins respectively on each of the right-handed plasmonic devices, it is therefore possible to determine a dissymmetry/asymmetry factor, $\Delta\Delta\lambda$, for each of the four proteins from ORD spectra, thereby enabling structural information about the four proteins to be determined. This is an example of multiplexing measurements for four different proteins.

EXAMPLES

In the following Examples, a method of analysing a biological material using a plasmonic device as described below was used.

The plasmonic devices were covered with glass slides to create fluidic cells. The glass slides were secured in place using silicone for adhesion.

A buffer solution is first entered into a fluidic cell comprising a left-handed plasmonic device, and a fluidic cell comprising a right-handed plasmonic device. ORD measurements are taken. Then, a solution containing the buffer and a protein is entered into a fluidic cell comprising a left-handed plasmonic device, and a fluidic cell comprising a right-handed plasmonic device. The solution is left for an hour to allow the protein to adsorb to the plasmonic device. After an hour, or sufficient time for adsorption to have occurred, ORD measurements are taken.

$\Delta\lambda_R$ and $\Delta\lambda_L$ values are calculated from ORD measurements in the presence of buffer and protein, and the ORD measurements in the presence of just buffer. From these, a dissymmetry/asymmetry factor, $\Delta\Delta\lambda$, is calculated.

In Examples 1 and 2, plasmonic devices were used in which the distance from the reference upper surface of the base substrate to the nanostructure upper surface in the thickness direction, was 80 nm. The area footprint of each chiral nanostructure was 0.20 $\mu m^2$. The chiral nanostructures were arranged in a square lattice array, with a lattice constant of 700 nm. In Example 1, an Au electrically conductive layer with a thickness of 100 nm was used. In Example 2, an Au electrically conductive layer with a thickness of 30 nm was used.

ORD measurements were taken for the plasmonic devices in the presence of a solution of Tris-HCl buffer only, and then in the presence of a solution of buffer and Concanavalin A (Con A), a high β-sheet content protein.

The amount of Con A used was approximately 251 picograms, as estimated from calibration using surface plasmon resonance measurements on an unstructured Au surface.

Figure 14A:
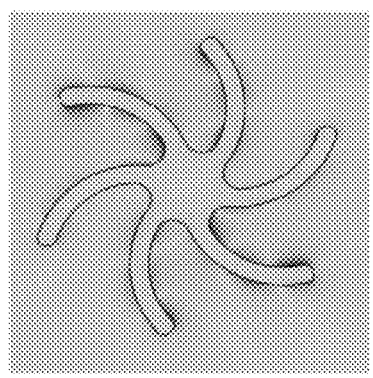
FIG. 14A shows chirality factor in a chiral nanostructure of a plasmonic device with a 100 nm film thickness.
Figure 14B:
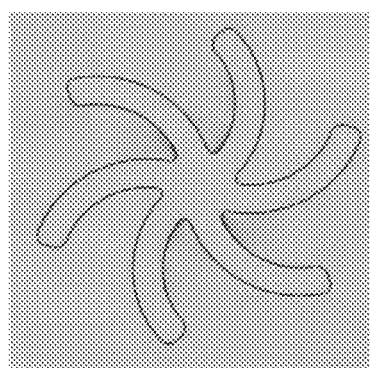
FIG. 14B shows chirality factor in a chiral nanostructure of a plasmonic device with a 30 nm film thickness.

FIG. 14A-B show the calculated chirality in a chiral nanostructure of a plasmonic device, normalized to the chirality of circularly polarized light, for the 100 nm film thickness (14A) and 30 nm film thickness (14B). As can be clearly seen from these figures, the chiral nanostructure with a 100 nm film thickness has a far higher chirality.

Figure 15A:
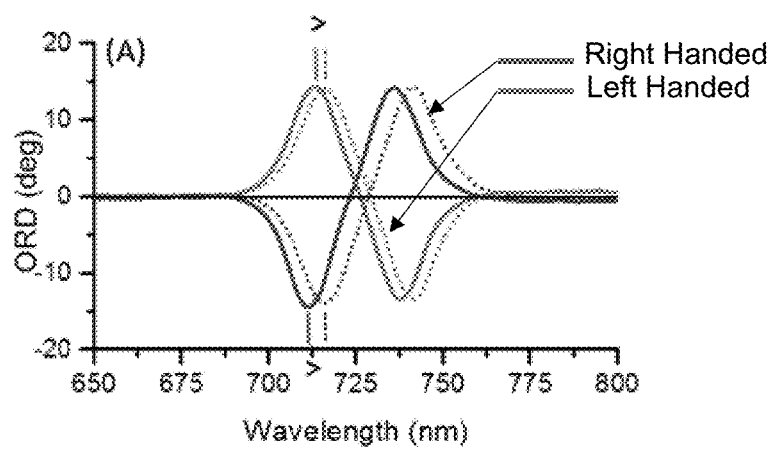
FIG. 15A shows ORD spectra as a function of wavelength, for plasmonic devices with a 100 nm film thickness, in the presence of buffer only, and in the presence of buffer and Concanavalin A.
Figure 15B:
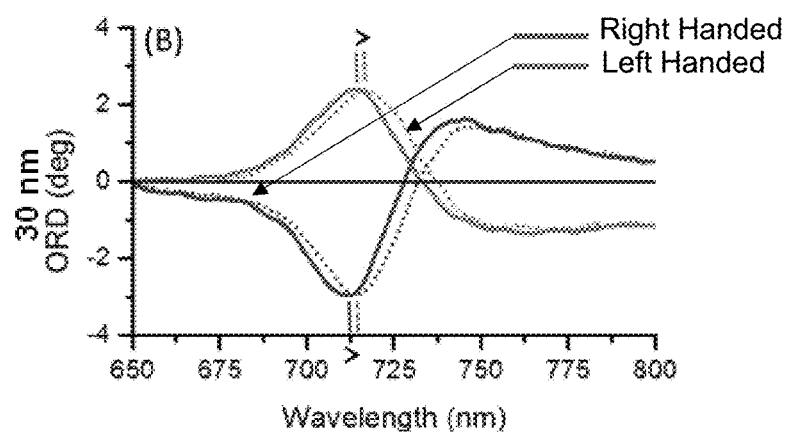
FIG. 15B shows ORD spectra as a function of wavelength, for plasmonic devices with a 30 nm film thickness, in the presence of buffer only, and in the presence of buffer and Concanavalin A.

FIG. 15A shows ORD spectra for the plasmonic devices with a 100 nm film thickness, in the presence of buffer only (solid line) and in the presence of buffer and Con A (dashed line), on left-handed and right-handed plasmonic devices. FIG. 15B shows the ORD spectra for the plasmonic devices with a 30 nm film thickness, in the presence of buffer only (solid line) and in the presence of buffer and Con A (dashed line), on left-handed and right-handed plasmonic devices.

The dissymmetry/asymmetry factor in the case of the 100 nm film thickness, was 1.9±0.2 nm. The dissymmetry/asymmetry factor in the case of the 100 nm film thickness, was 0.2±0.4 nm. Hence, we see a significantly higher sensitivity to protein structure when a plasmonic device with a film thickness of 100 nm is used.

In Example 3, ORD measurements were taken using the same 100 nm plasmonic as were used in Examples 1 and 2. This time, the plasmonic devices were coated with three different poly-lysines, a polymeric amino acid.

Figure 16:
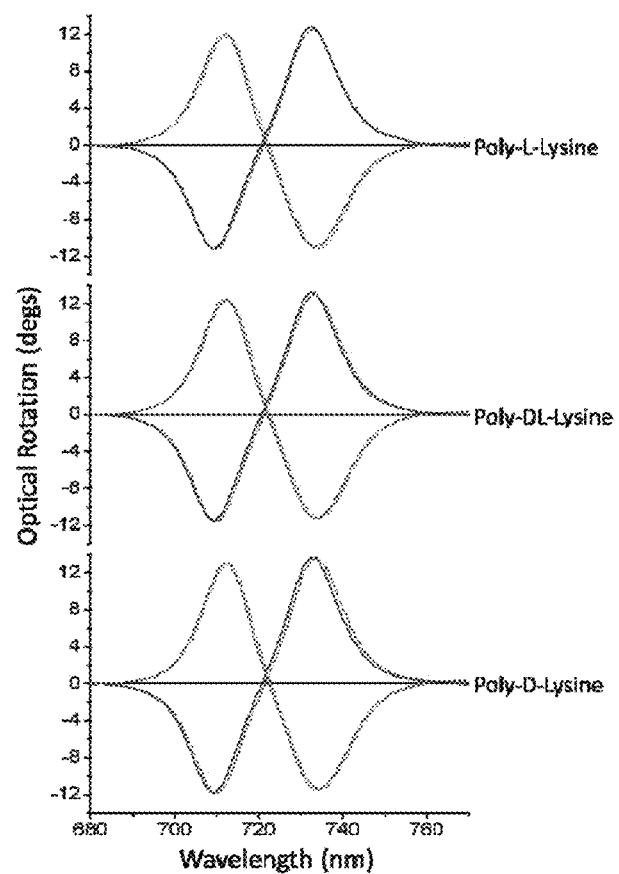
FIG. 16 shows ORD spectra from Example 3, with films of Poly-L-Lysine, Poly-DL-Lysine, and Poly-D-Lysine films were deposited.

Poly-lysine is a biocompatible cationic polymer which, when deposited from aqueous solution, reproducibly creates 1 nm thick films. Poly-L-Lysine, Poly-DL-Lysine, and Poly-D-Lysine films were deposited onto respective plasmonic nanostructures. The resulting ORD spectra are shown in FIG. 16, with solid lines showing the ORD spectra in the absence of chiral material, and the dashed lines showing ORD spectra in the presence of a poly-lysine.

Figure 17:
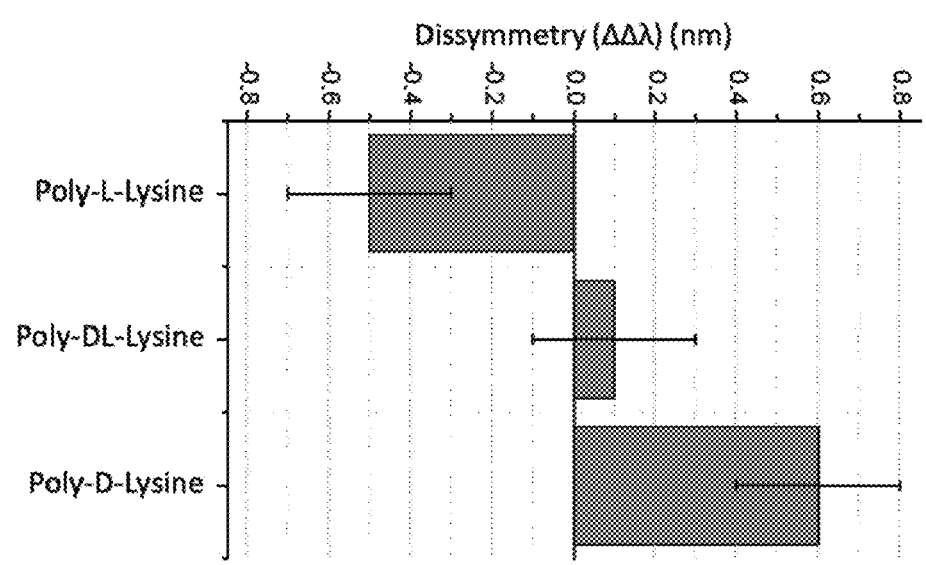
FIG. 17 shows dissymmetry/asymmetry factors (nm) for Poly-L-Lysine, Poly-DL-Lysine, and Poly-D-Lysine, as calculated from the ORD spectra of FIG. 15.

FIG. 17 shows, within error limits, equal and opposite dissymmetry for the Poly-L-Lysine and Poly-D-Lysine films respectively, and a zero dissymmetry for the Poly-DL-Lysine. These results conform to the expected result, based on the known structure of these polymers.

In Example 4, the same 100 nm plasmonic devices from Example 3 were used.

$\Delta\lambda_R$ and $\Delta\lambda_L$ values were again calculated from the difference between the ORD measurements in the presence of buffer and protein and the ORD measurements in the presence of just buffer.

Two proteins of the Shikimate pathway were used: 3-phosphate synthase (EPSPS), a 46 kDa molecular weight protein that binds glyphosate and shikimate-3-phosphate with low micromolar affinity; and Shikimate kinase (SK), a 19 kDa molecular weight protein that binds EDP and shikimic acid together with $Mg^{2+}$ ions with high micromolecular to low millimolecular affinity. Both of these proteins undergo ligand-induced conformational changes.

ORD measurements were taken in the presence of ligand only, protein only, and in the presence of both ligand and protein.

Figure 18:
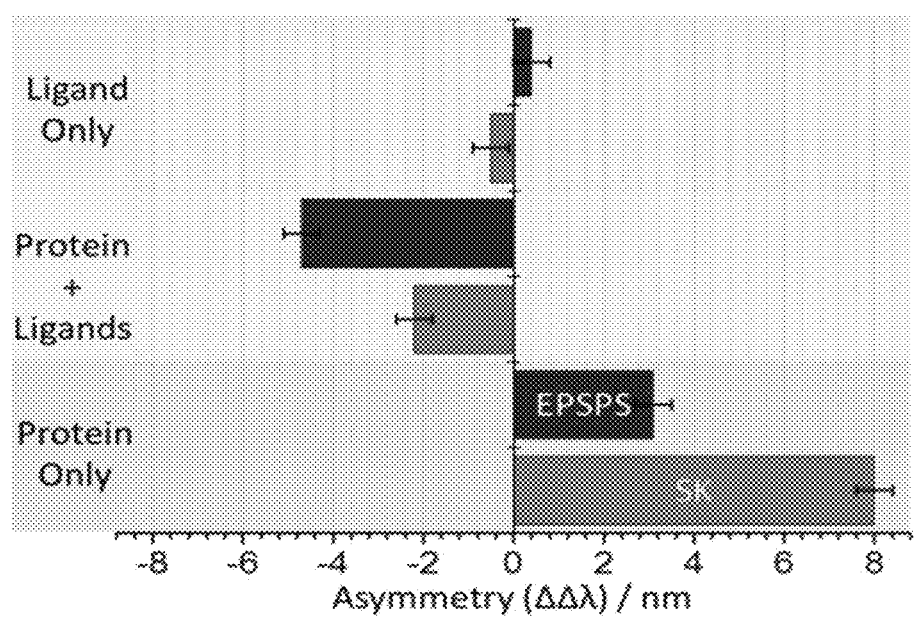
FIG. 18 shows the dissymmetry/asymmetry factors (nm) from Example 4, in the presence of ligands only, protein only, and in the presence of protein with bound ligands.

The results, in terms of dissymmetry/asymmetry factor $\Delta\Delta\lambda$, are shown in FIG. 18. The ligand solution used contained shikimic acid, ADP and shikimate-3-phosphate.

As can be clearly seen from FIG. 18, a significant difference in dissymmetry/asymmetry factor was bought about in the protein, by the presence of the ligands. Hence, we see that the plasmonic device of the present invention can be used to detect conformational changes in proteins, as caused by ligands.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

All references referred to above and/or below are hereby incorporated by reference in their entirety. Specifically, the following publications arising from the inventors' research groups are incorporated in their entirety:

Karimullah A S, Jack C, Tullius R, Rotello V M, Cooke G, Gadegaard N, Barron L D, Kadodwala M—Disposable Plasmonics: Plastic Templated Plasmonic Metamaterials with Tunable Chirality—Adv Mater. 2015 Oct. 7; 27(37): 5610-6

Tullius R, Karimullah A S, Rodier M, Fitzpatrick B, Gadegaard N, Barron L D, Rotello VM1, Cooke G, Lapthorn A, Kadodwala M.—"Superchiral" Spectroscopy: Detection of Protein Higher Order Hierarchical Structure with Chiral Plasmonic Nanostructures—J Am Chem Soc. 2015 Jul. 8; 137(26):8380-3

Jack C, Karimullah A S, Tullius R, Khorashad L K, Rodier M, Fitzpatrick B, Barron L D, Gadegaard N, Lapthorn A J, Rotello V M, Cooke G, Govorov A O, Kadodwala M—Spatial control of chemical processes on nanostructures through nano-localized water heating—Nat Commun. 2016 Mar. 10; 7:10946

REFERENCES

[1] J. N. J. Anker, W. P. Hall, O. Lyandres, N. N. C. Shah, J. Zhao, R. P. Van Duyne, *Nat. Mater.* 2008, 7, 8.

[2] J. K. Gansel, M. Thiel, M. S. Rill, M. Decker, K. Bade, V. Saile, G. von Freymann, S. Linden, M. Wegener, *Science* 2009, 325, 1513.

[3] J. B. Pendry, *Science* 2004, 306, 1353.

[4] V. M. Shalaev, *Nat. Plasmonics* 2007, 1, 41.

[5] E. Hendry, T. Carpy, J. Johnston, M. Popland, R. V Mikhaylovskiy, A. J. Lapthorn, S. M. Kelly, L. D. Barron, N. Gadegaard, M. Kadodwala, *Nat. Nanotechnol.* 2010, 5, 783.

[6] E. Hutter, J. H. Fendler, *Adv. Mater.* 2004, 16, 1685.

[7] J. R. L. Guerreiro, M. Frederiksen, V. E. Bochenkov, V. De Freitas, M. G. Ferreira Sales, D. S. Sutherland, *ACS Nano* 2014, 7958.

[8] P. K. Jain, X. Huang, I. H. El-Sayed, M. A. El-Sayed, *Plasmonics* 2007, 2, 107.

[9] K. L. Tsakmakidis, A. D. Boardman, O. Hess, *Nature* 2007, 450, 397.

[10] A. Vora, J. Gwamuri, N. Pala, A. Kulkarni, J. M. Pearce, D. Ö. Güney, *Sci. Rep.* 2014, 4, 4901.

[11] K. A. Willets, R. P. Van Duyne, *Annu. Rev. Phys. Chem.* 2007, 58, 267.

[12] X. Huang, P. K. Jain, I. H. El-Sayed, M. A. El-Sayed, *Lasers Med. Sci.* 2008, 23, 217.

[13] N. Liu, M. Hentschel, T. Weiss, A. P. Alivisatos, H. Giessen, *Science* 2011, 332, 1407.

[14] V. I. Belotelov, L. E. Kreilkamp, I. A. Akimov, A. N. Kalish, D. A. Bykov, S. Kasture, V. J. Yallapragada, A. Venu Gopal, A. M. Grishin, S. I. Khartsev, M. Nur-E-Alam, M. Vasiliev, L. L. Doskolovich, D. R. Yakovlev, K. Alameh, A. K. Zvezdin, M. Bayer, *Nat. Commun.* 2013, 4, 1.

[15] T. Cao, C. Wei, R. E. Simpson, L. Zhang, M. J. Cryan, *Sci. Rep.* 2014, 4, 4463.

[16] M. Matschuk, N. B. Larsen, *J. Micromechanics Microengineering* 2013, 23, 025003.

[17] K. Monkkonen, T. T. Pakkanen, J. Hietala, E. J. Paakkonen, P. Paakkonen, T. Jaaskelainen, T. Kaikuranta, Polym. Eng. Sci. 2002, 42, 1600.
[18] H. Sun, Microsyst. Technol. 2014, 21, 1.
[19] H. Pranov, H. K. Rasmussen, N. B. Larsen, N. Gadegaard, Polym. Eng. Sci. 2006, 46, 160.
[20] Y. Chen, J. Tao, X. Zhao, Z. Cui, A. S. Schwanecke, N. I. Zheludev, in Microelectron. Eng., 2005, pp. 612-617.
[21] A. C. Liou, R. H. Chen, Int. J. Adv. Manuf. Technol. 2006, 28, 1097.
[22] N. Gadegaard, M. J. Dalby, E. Martines, K. Seunarine, M. O. Riehle, A. S. G. Curtis, C. D. W. Wilkinson, Adv. Sci. Technol. 2006, 53, 107.
[23] E. Prodan, C. Radloff, N. J. Halas, P. Nordlander, Science 2003, 302, 419.
[24] M. Hentschel, T. Weiss, S. Bagheri, H. Giessen, Nano Lett. 2013, 13, 4428.
[25] J. Greener, R. Wimberger-Friedl, Precision Injection Molding: Process, Materials, and Applications, Hanser, 2006.
[26] J. M. Stormonth-Darling, R. H. Pedersen, C. How, N. Gadegaard, J. Micromechanics Microengineering 2014, 24, 075019.
[27] P. Lalanne, J. P. Hugonin, J. C. Rodier, Phys. Rev. Lett. 2005, 95, 1.
[28] H. Liu, P. Lalanne, X. Yang, J. P. Hugonin, IEEE J. Sel. Top. Quantum Electron. 2008, 14, 1522.
[29] B. Luk'yanchuk, N. I. Zheludev, S. A. Maier, N. J. Halas, P. Nordlander, H. Giessen, C. T. Chong, Nat. Mater. 2010, 9, 707.
[30] B. Gallinet, A. Lovera, T. Siegfried, H. Sigg, O. J. F. Martin, AIP Conf. Proc. 2012, 1475, 18.
[31] V. Giannini, Y. Francescato, H. Amrania, C. C. Phillips, S. A. Maier, Nano Lett. 2011, 11, 2835.
[32] P. Berini, Phys. Rev. B 2000, 61, 10484.
[33] S. A. Maier, Plasmonics: Fundamentals and Applications, Springer U S, 2007.
[34] C. W. Deutsche, D. A. Lightner, R. W. Woody, A. Moscowitz, Annu. Rev. Phys. Chem. 1969, 20, 407.
[35] L. D. Barron, Molecular Light Scattering and Optical Activity, Cambridge University Press, New York, 2009.
[36] X. Yin, M. Schäferling, B. Metzger, H. Giessen, Nano Lett. 2013, 13, 6238.
[37] P. W. Atkins, R. S. Friedman, Molecular Quantum Mechanics: An Introduction to Quantum Chemistry, Oxford University Press, New York, 2011.
[38] J. Anker, W. Hall, O. Lyandres, N. Shah, Nat. Mater. 2008, 7, 8.
[39] V. K. Valev, J. J. Baumberg, C. Sibilia, T. Verbiest, Adv. Mater. 2013, 25, 2517.
[40] E. Hendry, R. V Mikhaylovskiy, L. D. Barron, M. Kadodwala, T. J. Davis, Nano Lett. 2012, 12, 3640.
[41] P. Johnson, R. Christy, Phys. Rev. B 1972, 1318.

The invention claimed is:

1. A plasmonic device comprising:
a base substrate formed from a polymer material, and
an electrically conductive film formed on the base substrate;
wherein the base substrate has;
 a reference upper surface; and
 an arrangement of chiral nanostructures formed in relief from the reference upper surface;
 each chiral nanostructure having a nanostructure upper surface which is disposed at a distance of at least 30 nm from the reference upper surface in a thickness direction, wherein the chiral nanostructures formed in relief are formed as one of;
  (i) indentations in the reference upper surface, with the nanostructure upper surface recessed from the reference upper surface; and
  (ii) protrusions from the reference upper surface, with the nanostructure upper surface protruding from the reference upper surface; and
wherein the electrically conductive film is formed continuously on the nanostructure upper surface of each chiral nanostructure and on at least part of the reference upper surface of the base substrate with part of the electrically conductive film forming an electrical connection between the electrically conductive film on the nanostructure upper surface and the electrically conductive film on the said at least part of the reference upper surface.

2. The device of claim 1, wherein the chiral nanostructures are formed as indentations in the reference upper surface.

3. The plasmonic device of claim 1, wherein the electrically conductive film has a substantially uniform thickness.

4. The plasmonic device of claim 1, wherein the thickness of the electrically conductive film is less than the distance between the nanostructure upper surface and the reference upper surface.

5. The plasmonic device of claim 1, wherein thickness of the electrically conductive film is 50% or more of the distance between the nanostructure upper surface and the reference upper surface.

6. The plasmonic device of claim 1, wherein the thickness of the electrically conductive film is greater than the distance between the nanostructure upper surface and the reference upper surface.

7. The plasmonic device of claim 1, wherein the arrangement of chiral nanostructures consists of same-handedness chiral nanostructures.

* * * * *